US006882939B2

(12) United States Patent
Homans et al.

(10) Patent No.: US 6,882,939 B2
(45) Date of Patent: Apr. 19, 2005

(54) RAPID DETERMINATION OF PROTEIN GLOBAL FOLDS

(75) Inventors: Steven W. Homans, Leeds (GB); Alexander Giesen, Otley (GB)

(73) Assignee: ProSpect Pharma, Columbia, MD (US)

( * ) Notice: Subject to any disclaimer, the term of this patent is extended or adjusted under 35 U.S.C. 154(b) by 197 days.

(21) Appl. No.: 10/164,716

(22) Filed: Jun. 10, 2002

(65) Prior Publication Data

US 2003/0088364 A1 May 8, 2003

Related U.S. Application Data

(63) Continuation-in-part of application No. 09/983,020, filed on Oct. 22, 2001.
(60) Provisional application No. 60/241,841, filed on Oct. 20, 2000.

(51) Int. Cl.[7] .......................... G06F 17/11; G06F 17/50; G06F 19/00
(52) U.S. Cl. ........................... 702/19; 702/27; 364/496; 364/578
(58) Field of Search ..................................... 702/19, 27

(56) References Cited

U.S. PATENT DOCUMENTS

| 5,817,474 A | 10/1998 | Brown |
| 6,111,066 A | 8/2000 | Anderson, III et al. |
| 6,335,196 B1 | 1/2002 | Anderson, III et al. |
| 6,340,578 B1 | 1/2002 | Anderson, III et al. |

OTHER PUBLICATIONS

Al–Hashimi et al J. Magnetic Resonance, 2000, vol. 143, 402–406.*
Mueller, G. et al Journal of Molecular Biology 2000, vol. 300(1), pp. 197–212.*
Ramirez et al., "Modulation of the Alignment Tensor of Macromolecules Dissolved in a Dilute Liquid Crystalline Medium," *J. Am. Chem. Soc.* 120:9106–9107, 1998.
Tjandra, et al., "Magnetic Field Dependence of Nitrogen–Proton J Splittings in $^{15}$N–Enriched Human Ubiquitin Resulting from Relaxation . . . ," *J. Am. Chem. Soc.*, 118:6264–6272, 1996.
Bax et al., "High–Resolution Heteronuclear NMR of Human Ubiquitin in an Aqueous Liquid Crystalline Medium," *J. Biomol. NMR*, 10:289–292, 1997.
Losonczi et al., "Improved Dilute Bicelle Solutions for High–Resolution NMR of Biological Macromolecules," *J. Biomol. NMR*, 12:447–451 1998.
Prosser et al., "Use of a Novel Aqueous Liquid Crystalline Medium for High–Resolution NMR of Macromolecules in Solution," *J. Am. Chem. Soc.* 120:11010–11011, 1998.
Clore et al., "Measurement of Residual Dipolar Couplings of Macromolecules Aligned in the Nematic Phase of a Colloidal . . . ," *J. Am. Chem. Soc.* 120:10571–10572, 1998.
Hansen et al., "Tunable Alignment of Macromolecules by Filamentous Phage Yields Dipolar Coupling Interactions," *Nature Structural Biology* 5(12):1065–1074, 1998.
Kiddle et al., "Residual Dipolar Couplings as New Conformational Restraints in Isotopically $^{13}$C–Enriched Oligosaccharides," *FEBS Letters* 436:128–130, 1998.

(Continued)

Primary Examiner—Michael Borin
(74) Attorney, Agent, or Firm—Rothwell, Figg, Ernst & Manbeck P.C.

(57) ABSTRACT

This invention provides a method for rapidly obtaining accurate three-dimensional structure of proteins including large or multi-sub unit proteins, using a combination of NMR analysis of backbone only $^{13}$C, $^{15}$N or $^{13}$C and $^{15}$N isotopically labeled proteins which are optionally also $^{2}$H isotopically labeled in the Cα position protons and residual dipolar coupling measurements in more than one partially aligned state and/or orientation data pertaining to overlapping successive peptide pairs.

15 Claims, 22 Drawing Sheets

OTHER PUBLICATIONS

Wang et al., "A Liquid Crystalline Medium for Measuring Residual Dipolar Couplings Over a Wide Range of Temperatures," *J. Biomol. NMR*, 12:443–446, 1998.

Ottiger et al., "Bicelle–Based Liquid Crystals for NMR–Measurement of Dipolar Couplings at Acidic and Basic pH Values," *J. Biomol. NMR*, 13:187–191, 1999.

Fleming et al., "Cellulose Crystallites: A New and Robust Liquid Crystalline Medium for the Measurement of Residual Dipolar Couplings," *J. AM. Chem. Soc.* 122:5224–5225, 2000.

Rückert et al., "Alignment of Biological Macromolecules in Novel Nonionic Liquid Crystalline Media for NMR Experiments," *J. Am. Chem. Soc.* 122:7793–7797, 2000.

Mueller et al., "A Method for Incorporating Dipolar Couplings Into Structure Calculations in Cases of (Near) Axial Symmetry of Alignment," *J. Biomol. NMR* 18:183–188, 2000.

Hus et al., "De Novo Determination of Protein Structure by NMR Using Orientational and Long–Range Order Restraints," *J. Mol. Biol.* 298:927–936, 2000.

Tjandra et al., "Use of Dipolar $^1H$–$^{15}N$ and $^1H$–$^{13}C$ Couplings in the Structure Determination of Magnetically Oriented Macromolecules in Solution," *Nature Struct. Biol.* 4(9):732–738, 1997.

Wang et al., "Simultaneous Measurement $^1H$–$^{15}N$, $^1H$–$^{13}C'$ and $^{15}N$–$^{13}C'$ Dipolar Couplings in a Perdeuterated 30 kDA Protein Dissolved in a Dilute Liquid Crystalline Phase," *J. Am. Chem. Soc.* 120:7385–7386, 1998.

Ottiger et al., "Measurement of J and Dipolar Couplings from Simplified Two–Dimensional NMR Spectra," *J. Magn. Reson.* 131:373–378, 1998.

Lerche et al., "Pulse Sequences for Measurement of One–Bond $^{15}N$–$^1H$ Coupling Constants in the Protein Backbone," *J. Magn. Reson.* 140:259–263, 1999.

Tjandra et al., "Measurement of Dipolar Contributions to $^1JCH$ Splittings from Magnetic–Field Dependence of J Modulation in Two–Dimensional NMR Spectra," *J. Magn. Reson.* 124:512–515, 1997.

Clore et al., "Direct Structure Refinement Against Residual Dipolar Couplings in the Presence of Rhombicity of Unknown Magnitude," *J. Magn. Reson.* 131:159–162, 1998.

Clore et al., "A Robust Method for Determining the Magnitude of the Fully Asymmetric Alignment Tensor of Oriented Macromolecules in the Absence of Structural Information," *J. Magn. Reson.* 133:216–221, 1998.

Clore et al., "Impact of Residual Dipolar Couplings on the Accuracy of NMR Structures Determined from a Minimal Number of NOE Restraints," *J. Am. Chem. Soc.* 121:6513–6514, 1999.

Beger et al., "Protein $\phi$ and $\psi F0$ Dihedral Restraints Determined from Multidimensional Hypersurface Correlations of Backbone Chemical Shifts and their Use in the Determination of Protein Tertiary Structures," *J. Biomol. NMR* 10:129–142, 1997.

Ottiger et al., "Determination of Relative N–$H^N$, N–C', $C^\alpha$–C', and $C^\alpha$–$H^\alpha$ to Effective Bond Lengths in a Protein by NMR in a Dilute Liquid Crystalline Phase," *J. Am. Chem. Soc.* 120:12334–12341, 1998.

Ikura et al., "A Novel Approach for Sequential Assignment of $^1H$, $^{13}C$, and $^{15}N$ Spectra of Larger Proteins: Heteronuclear Triple–Resonance Three–Dimensional NMR Spectroscopy," *Biochemistry* 29:4659–4667, 1990.

Brünger, X–PLOR version 3.1: "A system for X–Ray Crystallography and NMR", Yale University Press, New Haven, CT., v–xv,1987.

Losonczi et al., "Order Matrix Analysis of Residual Dipolar Couplings Using Singular Value Decomposition," *J. Magn. Reson.* 138:334–342, 1999.

Tolman et al., "Nuclear Magnetic Dipole Interactions in Field–Oriented Proteins: Information for Structure Determination in Solution", *Proc. Natl. Acad. Sci. USA* 92:9279–9283, 1995.

Tjandra et al., "Direct Measurement of Distances and Angles in Biomolecules by NMR in a Dilute Liquid Crystalline Medium," *Science* 278:1111–1113, 1997.

Fowler et al., "Rapid Determination of Protein Folds Using Residual Dipolar Couplings," *J. Mol. Biol.* 304:447–460, 2000.

Hus et al., "Determination of Protein Backbone Structure Using Only Residual Dipolar Couplings," *J. Am. Chem. Soc.* 123:1541–1542, 2001.

Al–Hashimi et al., "Variation of Molecular Alignment as a Means of Resolving Orientational Ambiguities in Protein Structures from Dipolar Coupling," *J. Magn. Reson.* 143:402–406, 2000.

Mueller et al., "Global Folds of Proteins with Low Densities of NOEs Using Residual Dipolar Couplings: Application to the 370–Residue Maltodextrin–Binding Protein," *J. Mol. Biol.* 300:197–212, 2000.

McEvoy, Megan M., et al., "Nuclear Magnetic Resonance Assignments and Global Fold of a Chey–binding Domain in CheA, the Chemotaxis–Specific Kinase of *Escherichia Coli,*" *Biochemistry* 34(42):13871–13880, 1995. (Abstract).

Battiste, John L., et al., "Utilization of Site–Directed Spin Labeling and High–Resolution Nuclear Magnetic Resonance for Global Fold Determination of Large Proteins with Limited Nuclear Overhauser Effect Data," *Biochemistry* 39(18):5355–5365, May 9, 2000.

\* cited by examiner

Generate Linear
amino-acid chain

Calculate $\phi, \psi$ angles
for each peptide pair
using experimental
residual dipolar couplings Fold Linear sequence
with dihedral angle
and backbone NOE
restraints Refine structure
using NOE and
dipolar coupling
restraints

FIGURE 7

RAPID DETERMINATION OF PROTEIN GLOBAL FOLDS

This application is a continuation-in-part of copending U.S. application Ser. No. 09/983,020, filed Oct. 22, 2001, which claims priority from prior U.S. provisional application Ser. No. 60/241,841, filed Oct. 20, 2000 now abandoned.

BACKGROUND OF THE INVENTION

1. Technical Field

This invention relates to a protocol for the rapid determination of protein structure. In particular, the invention provides a method for rapidly obtaining protein or peptide structural information using only about 20–25% of the data set normally required in prior methods with a high degree of accuracy. The method allows the process to be automated to achieve results with a savings of time and labor.

2. Description of the Background Art

The determination of protein secondary, tertiary and quaternary structure is important in analyzing structural and functional relationships between all types of ligands and their receptors, enzymes and their substrates, or of any protein. For example, protein structure determination of a particular receptor generally can assist in rational drug design efforts to discover or synthesize more potent ligands at that receptor, or to design ligands with different activity profiles. Thus, existing pharmaceutical agents may be improved or changed to alter activity using detailed protein structural information. In addition, new chemical agents useful for treating disease can be developed using detailed structural information about receptors or other proteins in solution, receptors bound with ligand, or both.

X-ray crystallography is widely used to obtain detailed structural information about proteins and can provide the complete tertiary structure (global fold) of the backbone of a protein. This method, however, has several disadvantages. For example, only proteins which can be crystalized may be studied using X-ray crystallography. Some proteins are very difficult or impossible to crystalize. Moreover, crystalization can be very time consuming and expensive. Another major disadvantage of this method is that the structural information obtained is pertinent to the crystalline structure of the protein rather than the structure of the protein in solution. The bond angles present in a crystal structure may not be the same as those of the protein when it is in its active conformation and therefore may not provide information relevant to the biological or physiological system of interest.

Protein structure determination by high resolution multinuclear NMR also has become well known. In principle, this method gives all the information needed to determine the structure of a protein. Practically, however, the method is extremely time-consuming. In addition, in the past it has been very difficult to obtain accurate information about the structure of large proteins, for example 30–40 kilodaltons and especially 50 kilodaltons or larger using this method.

Traditional methods for the determination of protein structure using NMR utilized distance data derived from NOE spectra. Very recently, residual dipolar couplings have become established as additional conformational restraints in the determination of the solution structures of proteins via high resolution multinuclear NMR. Tolman et al., *Proc. Natl. Acad. Sci. USA* 92:9270–9283, 1995; Tjandra et al., *J. Am. Chem. Soc.* 118:6264–6272, 1996; Tjandra and Bax, *Science* 278:1111–1114, 1997; Bax and Tjandra, *J. Biomol. NMR* 10:289–292. The introduction of a number of lyotropic dilute liquid-crystalline solutions and other methods for weak macromolecular alignment has enabled straightforward measurement of these couplings for a variety of macromolecules. See Bax and Tjandra, *J. Biomol. NMR* 10:289–292, 1997; Losonczi et al., *J. Biomol. NMR* 12:447–451, 1998; Prosser et al., *J. Am. Chem. Soc.* 120:11010–11011, 1998; Clore et al., *J. Am. Chem. Soc.* 120:10571–10572, 1998; Hansen et al., *Nature Str. Biol.* 5:1065–1074, 1998; Kiddle and Homans, *FEBS Lett.* 436:128–130, 1998; Wang et al., *J. Biomol. NMR* 12:443–446, 1998; Ottinger and Bax, *J. Biomol. NMR* 13:187–191, 1999; Fleming et al., *J. Am. Chem. Soc.* 122:5224–5225, 2000; Ruckert and Otting, *J. Am. Chem. Soc.* 122:7793–7797, 2000.

Recently, interest has developed in the rapid determination of protein structural information based on residual dipolar couplings. Mueller et al. have developed a methodology for orienting peptide planes using dipolar couplings which determined the global fold of maltose binding protein in complex with β-cyclodextrin. This gave rise to pairwise RMSD (root mean square deviation) values between N- and C-terminal domains of the NMR structure and the corresponding regions in the X-ray structure of 2.8 Å and 3.1 Å, respectively. Mueller et al., *J. Mol. Biol.* 300:197–212, 2000; Mueller et al., *J. Biomol. NMR* 18:183–188, 2000. Lower values indicate less variation in the calculations and a more accurate structure. Generally, any value greater than 3 Å is considered quite inaccurate. Therefore, improvements in the variation would be greatly desired.

Fowler et al. (*J. Mol. Biol.* 304:447–460, 2000) have utilized $N_i$—$H_i^N$, $H_i^N$—$H_{\alpha i}$, $H_i^N$—$H^N_{\alpha i\pm 1}$, $H_i^N$—$H^N_{i+1}$ residual dipolar couplings together with a small number of backbone-sidechain NOEs to determine the backbone fold of acyl carrier protein to an RMSD between backbone atoms of about 3 Å. Hus et al. (*J. Mol. Biol.* 298:927–936, 2000) have utilized long-range order restraints available from paramagnetic systems in combination with residual dipolar couplings to define the fold of cytochrome C' in the complete absence of NOE restraints. Very recently, this same group has determined the global fold of ubiquitin to 1.0 Å backbone RMSD (residues 1–71) with respect to the solution structure determined by conventional methods, using restraints derived solely from $N_{i+1}$—$H_{i+1}^N$, $C'_i$—$N_{i+1}$, $C'_i$—$H_{i+1}^N$, $C_i^\alpha$—$C'_i$, $C^\alpha$—$H^\alpha$ and $C^\alpha$—$C^\beta$ residual dipolar couplings in two independent tensor frames. Hus et al., *J. Am. Chem. Soc.* 123:1541–1542, 2001.

These methods of protein fold determination, however effective, have the major drawback of being difficult and time-consuming. Furthermore, the complexity of the calculations needed and the large number of data points makes determination of the global fold of large proteins difficult to obtain. This is due largely to the use of universally isotopically enriched material which yield split signals in the NMR spectrum, each of which need to be assigned before a structure determination can be commenced. Splitting of signals results in both more and weaker signals. This phenomenon causes overlap of signals and a far inferior signal-to-noise ratio, both of which make the assignment process more difficult and rule out automation of the process. Methods currently available therefore can provide accurate structures or provide some structural data relatively quickly and easily, but no methods for rapid determination of the global fold are available which can also achieve the degree of accuracy which is desired. The ability to automate the various steps in the process would be of great advantage in achieving both rapid and sufficiently accurate results, however this has not been possible using the available techniques.

SUMMARY OF THE INVENTION

This invention provides a method for rapidly determining the three-dimensional structure of a molecule having a peptidic sequence of three or greater amino acids, including large proteins of greater than 30 kilodaltons, 50 kilodaltons, or larger. The method overcomes what has been a fundamental problem in NMR spectroscopy and a barrier to obtaining useful structural information for a number of proteins.

Generally, the method involves subjecting the peptide or protein molecule to NMR analysis, assigning the molecule by computer based on the NMR analysis and measuring residual dipolar couplings of the protein in two different partially aligned states. The protein or peptide may be, for example, dissolved in two different liquid crystalline solutions or mechanically aligned. Liquid crystalline solutions are well known in the art. Therefore, a skilled person can easily select a suitable medium to impart partial alignment to the protein of interest. The invention is contemplated for use with any medium (such as a solvent or solution) or mechanical means which imparts partial alignment to the protein to be analyzed, including any suitable liquid crystalline medium.

Using the magnitudes and orientations of the principal axes of the alignment tensors, the orientation of dipeptide fragments of the protein are calculated with a computational algorithm. As a first step, the peptide or protein molecule is substituted on the backbone with $^{13}C$, $^{15}N$, or both $^{13}C$ and $^{15}N$ and the Cα position protons are optionally substituted with $^2H$. Measurement in two different partially aligned states, each of which provides a different order in two dimensions, facilitates great improvement in the ease of fold calculations.

The $\phi,\psi$ angles for a first amino acid of the protein are varied computationally in 15° steps. At each point, the rigid-body orientation (in terms of Euler angles) of the first amino acid and a second amino acid adjacent in the peptidic sequence to the first amino acid are minimized by the computer with respect to both tensor frames simultaneously and the minimum difference between measured and calculated dipolar couplings for each of the first and second amino acids are calculated. The $\phi,\psi$ angles having a minimum energy and hence the orientation of the dipeptide fragment of the larger peptide or protein sequence (composed of the first and second amino acids) having the minimum energy are derived from these calculated dipolar couplings. The steps are repeated for each sequential dipeptide fragment of the larger molecule to obtain the structure of the peptide or protein backbone. The same steps also may be repeated for each of the secondary structural elements as well. The result is global fold determination in days instead of months if this process is automated.

Accordingly, the invention provides a method for determining the global fold of a peptidic molecule having a sequence of three or greater amino acids which comprises the steps of (a) providing the molecule in a form which is substituted on the backbone with an isotope selected from the group consisting of $^{13}C$, $^{15}N$, and both $^{13}C$ and $^{15}N$; (b) subjecting the substituted molecule to NMR analysis in a non-aligned medium; (c) assigning the molecule by computer based on the NMR analysis; (d) placing the molecule in a first state of partial alignment and measuring residual dipolar couplings for the molecule in the first state of partial alignment, wherein the magnitudes and orientations of the principle axes of the alignment tensors for the first state of partial alignment are known or obtained; (e) placing the molecule in a second state of partial alignment and measuring residual dipolar couplings for the molecule in the second state of partial alignment, wherein the magnitudes and orientations of the principle axes of the alignment tensors for the second state of partial alignment are known or obtained; (f) varying computationally by increments the $\phi,\psi$ angles for a first amino acid of the molecule; (g) minimizing the rigid-body orientation of the first amino acid and a second amino acid adjacent in the peptidic sequence to the first amino acid with respect to both tensor frames simultaneously; (h) calculating the minimum difference between measured and calculated dipolar couplings for each of the first and second amino acids; (i) deriving the $\phi,\psi$ angles and orientation of the dipeptide fragment composed of the first and second amino acids; and (j) repeating steps (f)–(i) for each sequential dipeptide fragment of the molecule to obtain a global fold of the peptidic molecule. The method may further comprise repeating steps (f)–(i) for at least one secondary structural element. The invention also provides methods in which the peptidic molecule is further isotopically substituted with $^2H$ at the Cα position protons.

In a further embodiment, the invention provides methods which further comprise confirming that the $\phi,\psi$ angles derived in step (i) above are correct by matching the orientation of overlapping successive peptide pairs.

In yet a further embodiment, the invention provides methods wherein the residual dipolar couplings for the molecule are measured in step (d) above in at least two different media which impart a weak alignment to the molecule. The media may be liquid crystalline solutions.

In yet a further embodiment, the invention provides methods which further comprise additionally performing steps (b) through (j) using the peptidic molecule which has been universally isotopically substituted in one or more species of amino acid, or in one species of amino acid.

In yet a further embodiment, the invention provides a method as described above which further comprises refining the global fold of the peptidic molecule by including data concerning interatom distances, for example NOE data.

In yet a further embodiment, the methods use measurement of at least three residual dipolar couplings for each state of partial alignment, for example three, four, five, or more than five residual dipolar couplings.

In yet a further embodiment, the invention provides a structural map obtained by any of the methods described above.

BRIEF DESCRIPTION OF THE DRAWINGS

FIG. 6A shows the results from an intermediary calculation while FIG. 6B shows the results from the refined calculation.

FIG. 7 is a flow chart showing some of the steps disclosed for the method of obtaining global fold data.

DETAILED DESCRIPTION OF THE PREFERRED EMBODIMENTS

The methods described here enable automation of the assignment process and the rapid calculation of the structure of the protein backbone. This reduces the time taken for structural analysis of a protein by NMR from years or months to only a few days. Provided the protein to be studied can be purified, structural information can be achieved very rapidly for proteins of any size and type, and from any source.

Figure 1A:
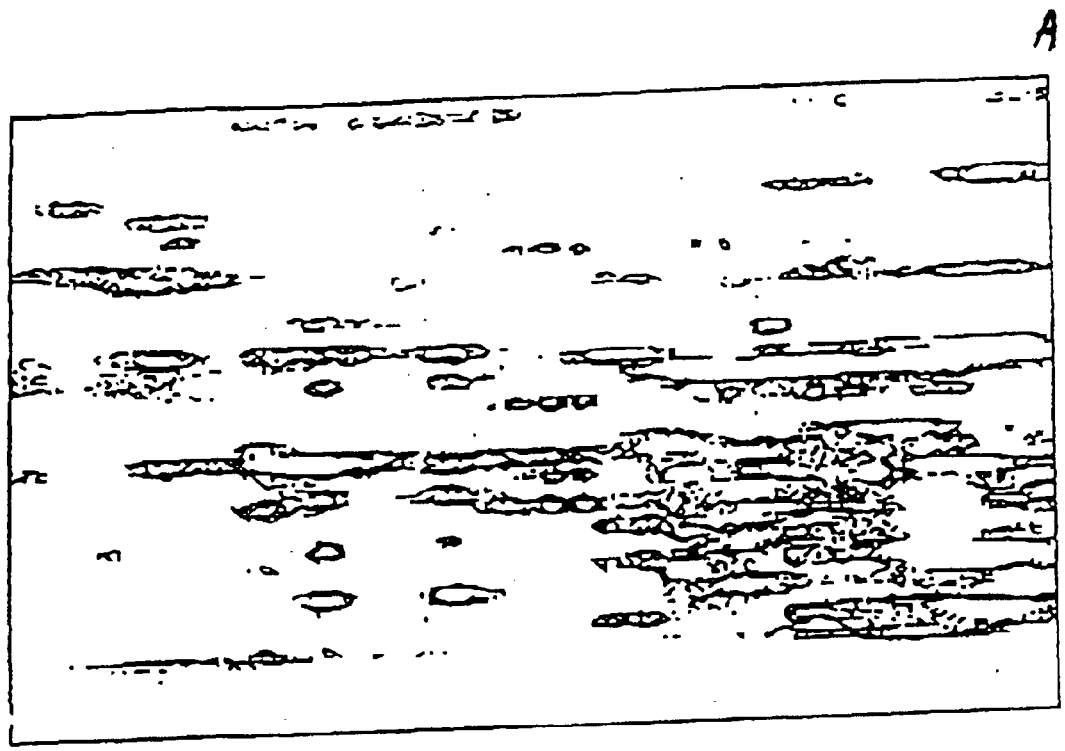
FIG. 1 shows NMR spectral data using conventional universal isotopic labeling of a protein (1A) and backbone only isotopic labeling of β-lactamase, a protein approximately twice the size (1B).
Figure 1B:
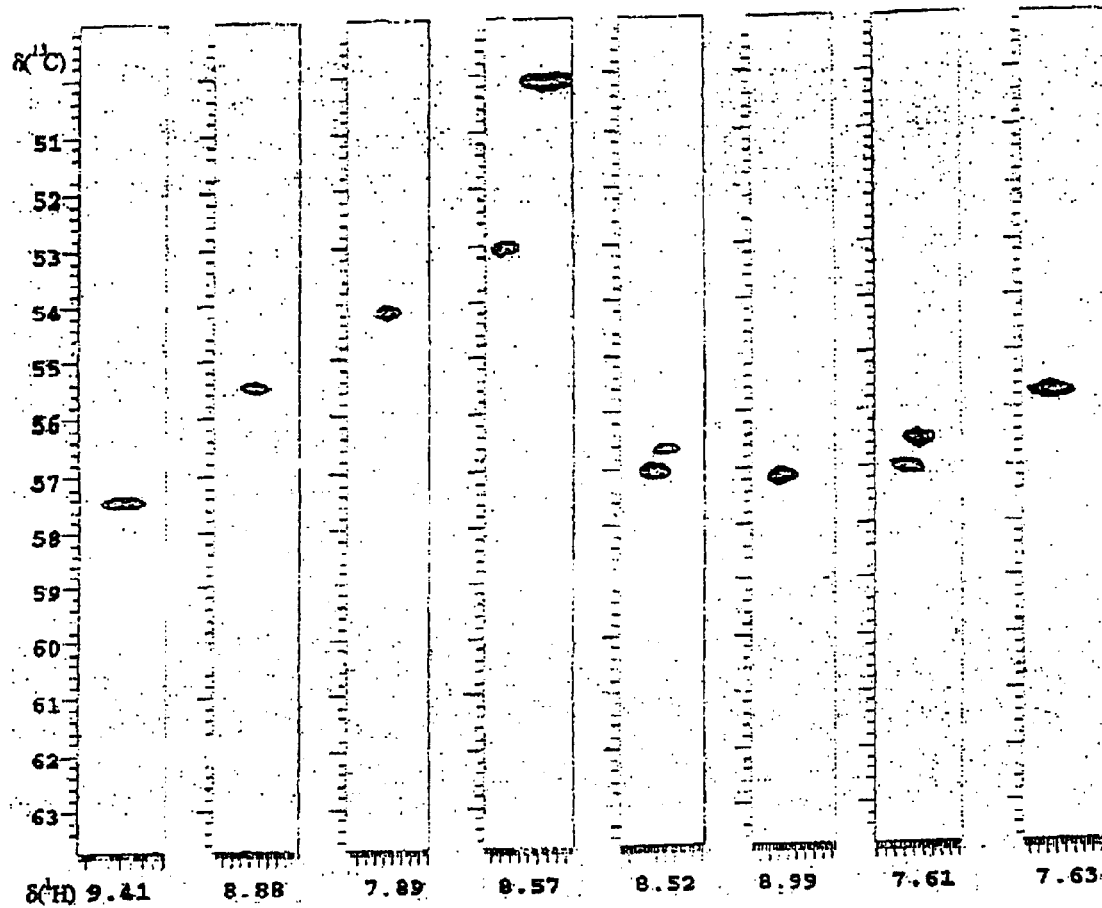

Incorporation of the stable isotopes $^{13}C$, $^{15}N$ into the backbone of the protein, but not the amino acid side chains (and optionally $^2H$ in the Cα position protons) eliminates the causes of poor spectral quality normally seen in NMR spectra of proteins, greatly simplifies assignment and allows the NMR techniques to focus on signals relevant to determining the global fold. See FIG. 1. Such backbone labeling of peptides and proteins may be achieved using the methods disclosed in U.S. Pat. No. 6,111,066, the disclosures of which are hereby incorporated by reference. Generally, the number of signals seen is reduced by a factor of four, while multiple signals are condensed into sharp singlets. Both these factors increase the signal to noise ratio and greatly reduce signal overlap. The greater quality of the spectra allows assignment of signals to be automated, which previously had not been possible. The inventive methods also allow very rapid protein global fold determination because the number of residual dipolar coupling restraints can be reduced while still providing good accuracy in global fold determination. These assigned signals can be used to calculate the global fold of the protein according to the methods of this invention.

Although the methods of this invention are suitable for the determination of structural information of any peptidic molecule of three or more amino acids in length, and therefore encompass both proteins and peptides, the description, for simplicity, will refer only to proteins. It is understood that the term "protein," in this application, refers to any peptidic molecule of three or greater amino acids. The methods are particularly useful for proteins of 20–30 kilodaltons or larger, which have been difficult to study using prior art methods, particularly proteins of 50 or 55 kilodaltons or more. Of course, smaller proteins and peptides may be studied using the inventive methods as well, including oligopeptides of three or greater amino acids.

According to this invention, the NMR spectrum of a protein is acquired with the protein in a partially aligned state. When non-spherical macromolecules, such as proteins, are dissolved in a dilute liquid-crystalline medium, for example, there is a small but significant and measurable tendency for the molecules to adopt a particular overall orientation (alignment) in the solution relative to the tensor frame of the particular liquid crystalline medium. As a result of this weak orientational tendency, residual dipolar couplings are discernable from the NMR spectrum of the macromolecule. Alternatively, the molecules can be dissolved in any solvent or solution which imparts a weak alignment to them. For example, it is known in the art to place proteins in a solution containing phage for NMR analysis. In addition, the molecules may be mechanically aligned, for example by dissolving in polyacrylamide gel or using physical pressure alignment. Although the description and examples below, for the sake of simplicity, refer to partial alignment in liquid crystalline solution, it is understood that any of the described methods alternatively may use partial alignment of the molecules by any suitable method, including partial alignment in other types of solutions or mechanically.

For a given chemical bond, for example the bond between a proton ($^1H$) and a carbon ($^{13}C$) nucleus, the size of the measured dipolar coupling depends on the orientation of the bond with respect to a coordinate frame which is sometimes referred to as the "principal axis system of the alignment tensor" or "tensor frame." Although the derivation of this tensor is complex, in its simplest form it is Cartesian coordinate system with the usual x, y and z axes:

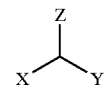

The dipolar coupling depends upon orientation according to Equation I:

$$D_{PQ}(\theta, \phi) = S\frac{\mu_o}{4\pi}\gamma_P\gamma_Q h\, A_a(3\cos^2\theta - 1) + \frac{3}{2}A_r\sin^2\theta\cos 2\phi / 4\pi^2 r_{PQ}^3$$

The dipolar coupling depends on the angles θ and φ, which define the orientation of the bond with respect to the principal axis system.

Calculation of θ and φ for each bond is performed by measuring the dipolar coupling by NMR and solving the above equation. However, due to the functional form of the equation, there are a minimum of eight solutions (i.e., eight θ,φ pairs) resulting from each dipolar coupling. Thus, for each bond there is an eight-fold ambiguity in its calculated position. The ambiguity in the total structure of a molecule increases exponentially (to the power of the number of bonds in the molecule). For a peptide or protein, this quickly results in a prohibitively large number of possible solutions. One way to resolve the ambiguity inherent in this equation is to measure dipolar coupling in a second tensor frame that orients the molecule differently. The molecule is therefore oriented along a second principal axis system non-coincident with the first. Under these circumstances, provided a sufficient number of dipolar couplings can be measured for a given molecular fragment, there is a single solution to the above Equation I. The bond angle is thus unambiguously determined. Fewer restraints are required to obtain the structure than methods using NOEs alone, so the method is able to provide results more quickly and easily. Without wishing to be bound by theory, only three residual dipolar couplings per tensor frame are required to obtain an accurate, unambiguous structure. It is contemplated that at least three residual dipolar couplings are measured per tensor frame, for example, 3, 4, 5, or more than 5 residual dipolar couplings.

Figure 2:
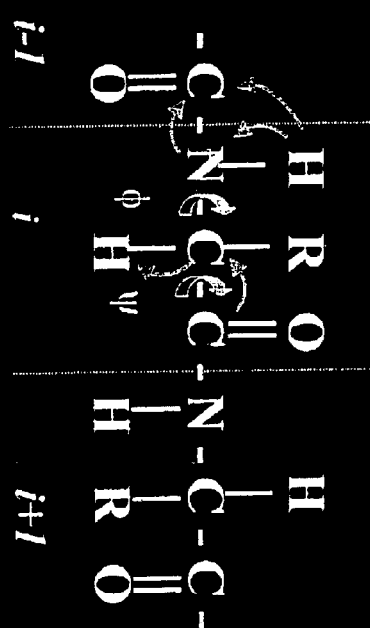
FIG. 2 is a schematic diagram of a protein fragment showing $\phi$ and $\psi$.

By walking along the protein backbone, two residues at a time, the relative orientations of each residue pair are sequentially determined. Thus, measuring the residual dipolar coupling data for each dipeptide fragment of the protein in two independent tensor frames (e.g., in two different liquid crystalline solutions) allows one to calculate the bond angles of each of the various bonds in the protein chain so that the global fold is obtained. See FIG. 2.

Figure 3:
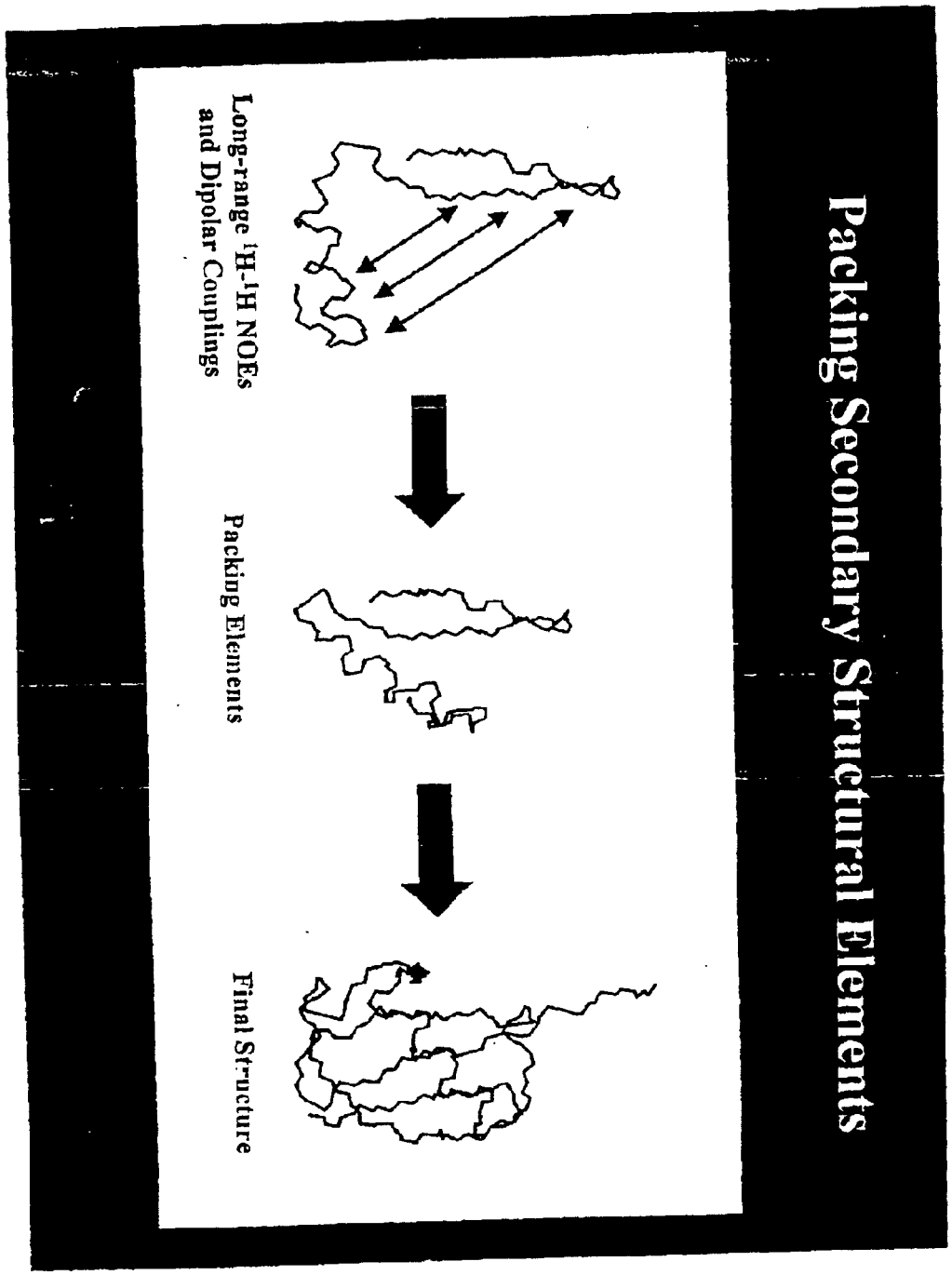
FIG. 3 is schematic diagram illustrating the refinement of a protein structure.

Mapping the structure of a protein using backbone dipolar couplings is achieved by varying, by computer, $\phi$ and $\psi$ bond angles by increments from 0° through 360°. Fifteen degree increments are sufficient, however it is contemplated that increments of about 15 to about 5 are preferred, for example, 12 degrees, 10 degrees, 8 degrees or 5 degrees. Three dimensional $\phi,\psi$ potential surfaces may be calculated using a suitable commercially available program such as, for example, XPLOR. Advantageously, an extended structure for the protein may be generated by setting all $\phi,\psi$ angles to 180° (with the exception of $\phi$ for prolines). Groups of three residues (i−1, i, i+1) then may be considered stepwise from the COOH terminus, with the sidechain of residue i truncated at $C^\beta$. The values of $\phi$ and $\psi$ for residue i may be varied independently through 360° in 15° increments, resulting a two dimensional grid of points. At each point, a rigid body minimization is performed on the tripeptide fragment to minimize the difference between experimental and theoretical residual dipolar couplings $N_i$—$H_i^N$, $N_{i+1}$—$H_{i+1}$, $C_i^\alpha$—$H_i^\alpha$, $H_i^N$—$C'_{i-1}$, $H_{i+1}^N$—$C'_i$ with respect to two sets of external Cartesian axes whose relative orientation is defined by the two tensor frame orientations. To overcome the effects of local minima during the minimization procedure, the rigid body minimization may be performed multiple times, for example about 5 to about 20 times or preferably about 10 times, at each grid point, starting with randomized values of the three Euler angles that describe the orientation of the tripeptide fragment in the tensor frames. The axial $A_\alpha$, component and rhombicity R (Bax, *Science* 278:1111–1114, 1997) in each tensor frame may be taken from published information or may be determined according to any known and convenient method. Force constants are used for N—$H^N$, $C^\alpha$—$H^\alpha$ and $H^N$—C' residual dipolar couplings, respectively. See Tjandra et al., *Nature Struct. Biol.* 4:732, 1997. In addition, a weak repulsive van der Waals term was included to account for steric clashes involving the $C^\beta$ atom of residue i. Use of such a van der Waals term is considered standard practice by those in the art and is well understood. Therefore, skilled persons can readily include a suitable van der Waals term. Commercially available programs generally include an option to use a van der Waals term. The resulting potential surfaces are contoured automatically using, for example, any conventional contour plotting algorithm such as gnuplot, which is available free over the internet, or any other convenient computer software. Structural elements determined by this method may be refined, if necessary, using a limited number of NOEs and assembled into a final structure. See FIG. 3.

Residual dipolar coupling data, measured in two independent tensor frames (two different states of partial alignment) for a given dipeptide fragment in a protein depend on five parameters: namely the backbone torsion angles $\phi$ and $\psi$ and the three Euler angles representing the orientation of the fragment in the tensor frame (assuming a fixed orientation of the peptide plane). With two tensors, the orientation of a chiral motif is completely defined. Ramirez et al., *J. Am. Chem. Soc.* 120:9106–9107, 1998; Wang et al., *J. Am. Chem. Soc.* 120:7385–7386, 1998; al-Hashimi et al., *J. Magn. Reson.* 143:402–406, 2000; Hus et al, *J. Am. Chem. Soc.* 123:1541–1542, 2001. The inventive method takes advantage of this to determine the global fold of a protein. To determine the structure of the complete protein in the minimum time, it is advantageous to use at least the three largest residual dipolar couplings that can readily be measured in proteins ($N_i$—$H_i^N$, $C_i\alpha$—$H_i^\alpha$ and $H_i^N$—$C'_{i-1}$). These couplings can be determined to reasonable accuracy using an 'IPAP' type approach without recourse to time-consuming J-modulation methods. Ottinger et al., *J. Magn. Reson.* 131:373–378, 1998; Lerche et al., *J. Magn. Reson.* 140:259–263, 1999; Tjandra and Bax, *J. Magn. Reson.* 124:513–515, 1997.

Tensor orientations of a dilute liquid crystalline solution or any other solution are readily available if the structure of a molecular fragment is known. In the absence of a known structure, models obtained from idealized secondary structure elements may be used in some cases, however large errors for the dipolar couplings have to be used to account for deviation of the actual structure of the molecular fragment from the idealized structure. Fowler et al. *Biophys. J.* 78:2827Pos, 2000. In unfavorable cases, where there is a significant deviation of the rigid structure used as a model and the actual structure of the molecular fragment, it is not possible to obtain any order tensor orientation from idealized structures. To work around this problem, a simulated annealing approach may be used to simultaneously refine an idealized starting structure to obtain the relative orientation of the order tensor frames. For example, the relative orientation of two tensor frames may be obtained using only $H^N$—N and $C\alpha H\alpha$ residual dipolar one-bond couplings from two different alignment media and an idealized $\alpha$-helix as starting structure.

Figure 4:
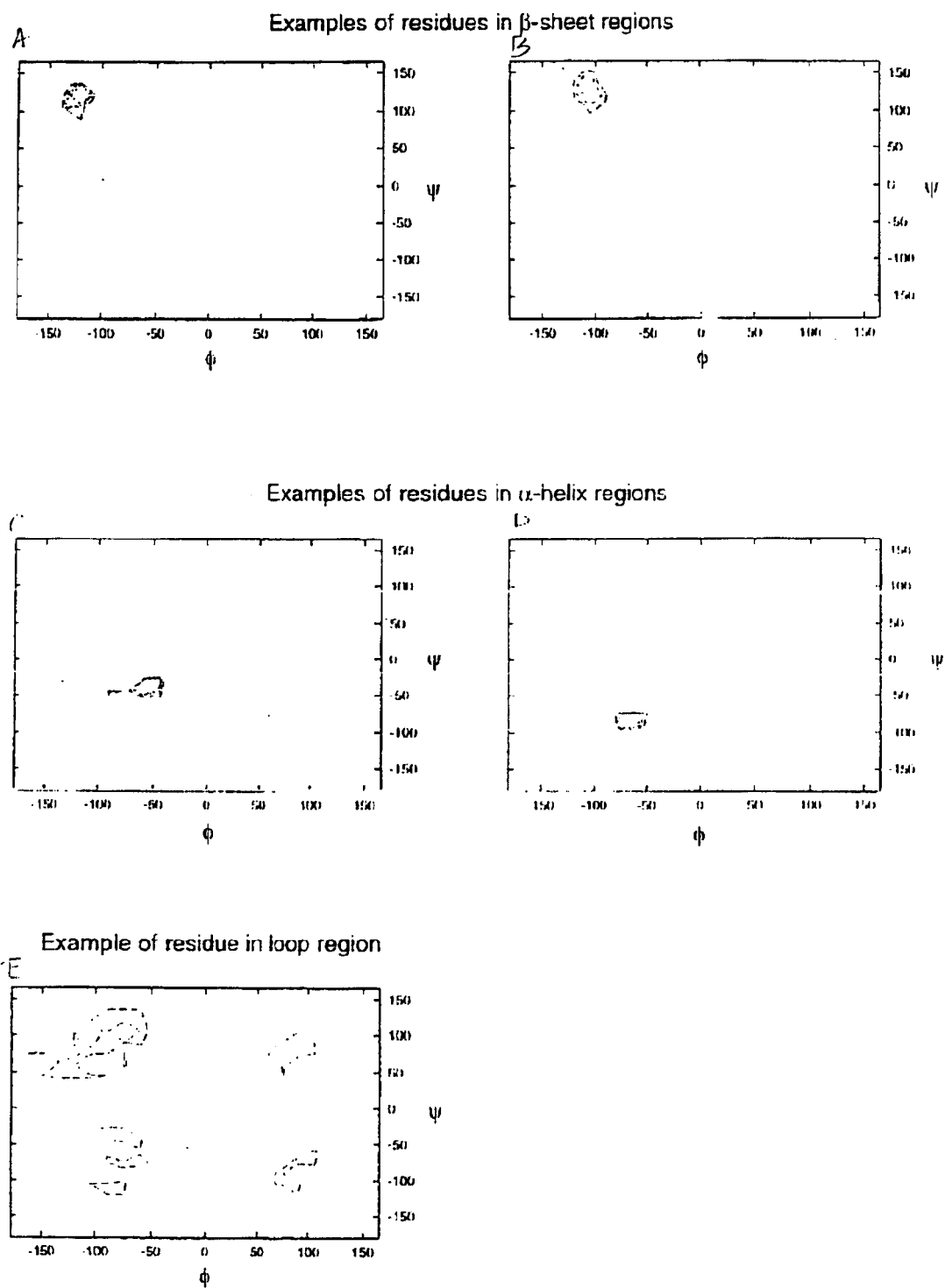
FIG. 4 is a group of contour maps providing examples of residues in β-pleated sheet, α-helix and loop regions of a protein.

Having the tensor parameters, global fold determination according to this invention first involves the derivation of $\phi,\psi$ values for each dipeptide fragment that is compatible with the measured dipolar couplings in each tensor frame. By analogy with the work of Wang et al., *J. Am. Chem Soc.* 120:7385–7386, 1998, this can be achieved by use of a grid-search over $\phi$ and $\psi$, while simultaneously optimizing the orientation of the dipeptide fragment relative to the two alignment tensors that gives the best fit between predicted and measured couplings. This can be achieved by incorporating residual dipolar couplings as pseudo-energy terms in a conventional energy minimization protocol. See Clore et al., *J. Magn. Reson.* 131:159–162, 1998; Clore et al., *J. Magn. Reson.* 133:216–221, 1998; Clore et al., *J. Am. Chem. Soc.* 121:6513–6514, 1999, the disclosures of which are hereby incorporated by reference. In addition, a van der Waals' repulsion term which includes all backbone plus $C^\beta$ atoms of each residue was added to account for steric clashes as discussed above. The resulting data can conveniently be analyzed as three dimensional potential energy surfaces of $\phi$ versus $\psi$ versus energy using freely available software programs such as, for example, gnuplot, which are known in the art. Selected contour maps derived from such a procedure are shown in FIG. 4 (ubiquitin).

The minimum difference between measured and calculated dipolar couplings for each of these two amino acid fragments gives experimentally derived $\phi,\psi$ angles and the orientation of the dipeptide fragment. Generally, unique values of the $\phi,\psi$ angles are found for regions of secondary structure in the protein, whereas multiple solutions may be found for loop regions (compare FIGS. 4A–4D with 4E). Multiple solutions for loop regions are not unexpected since loop regions usually are mobile in proteins. The only other angle defining protein backbone conformation, $\omega$, is invariably 180° due to planarity of the peptide group.

Figure 5:
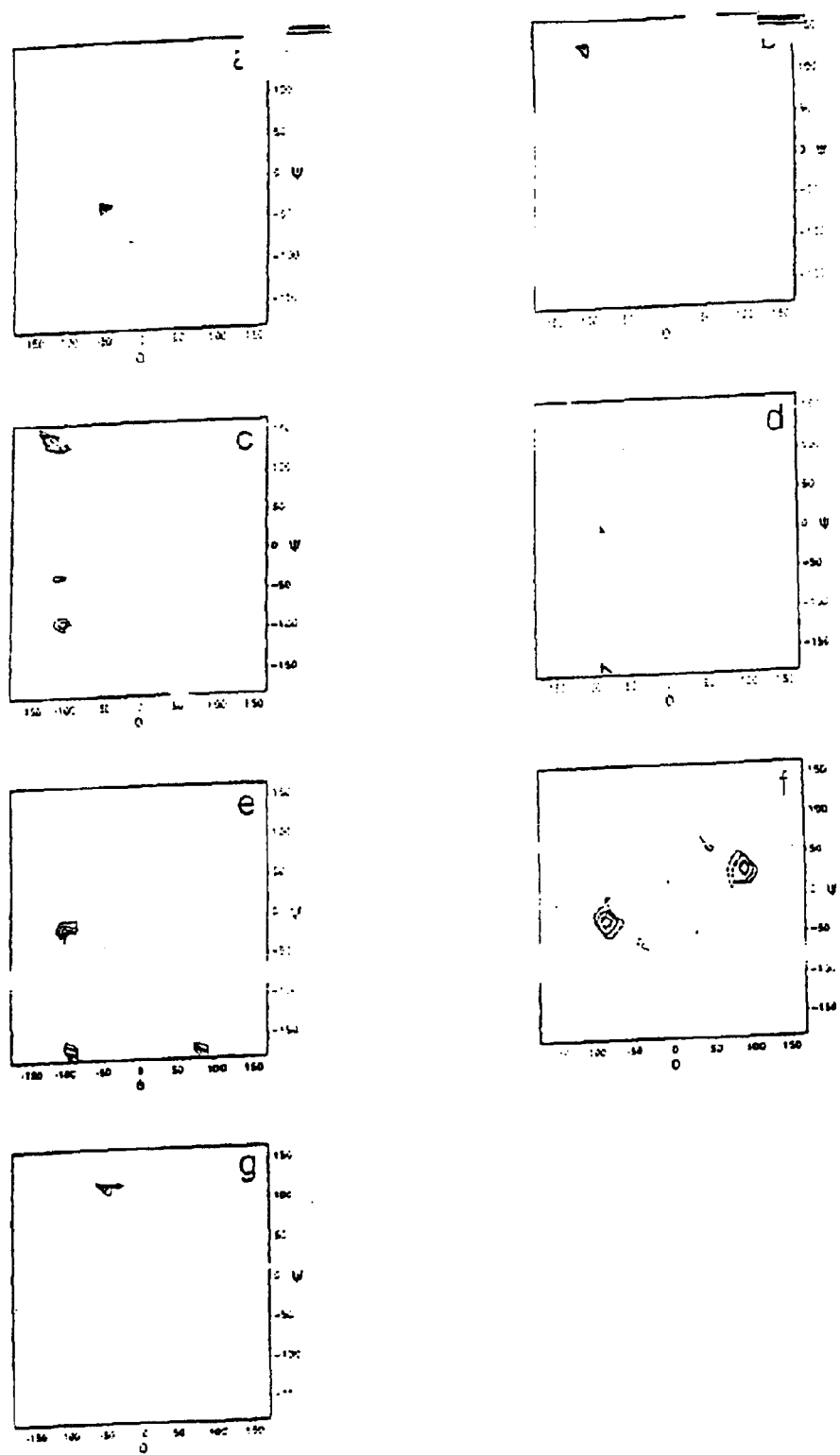
FIG. 5 is a group of contour maps providing data for selected residues of ubiquitin.
Figure 6:
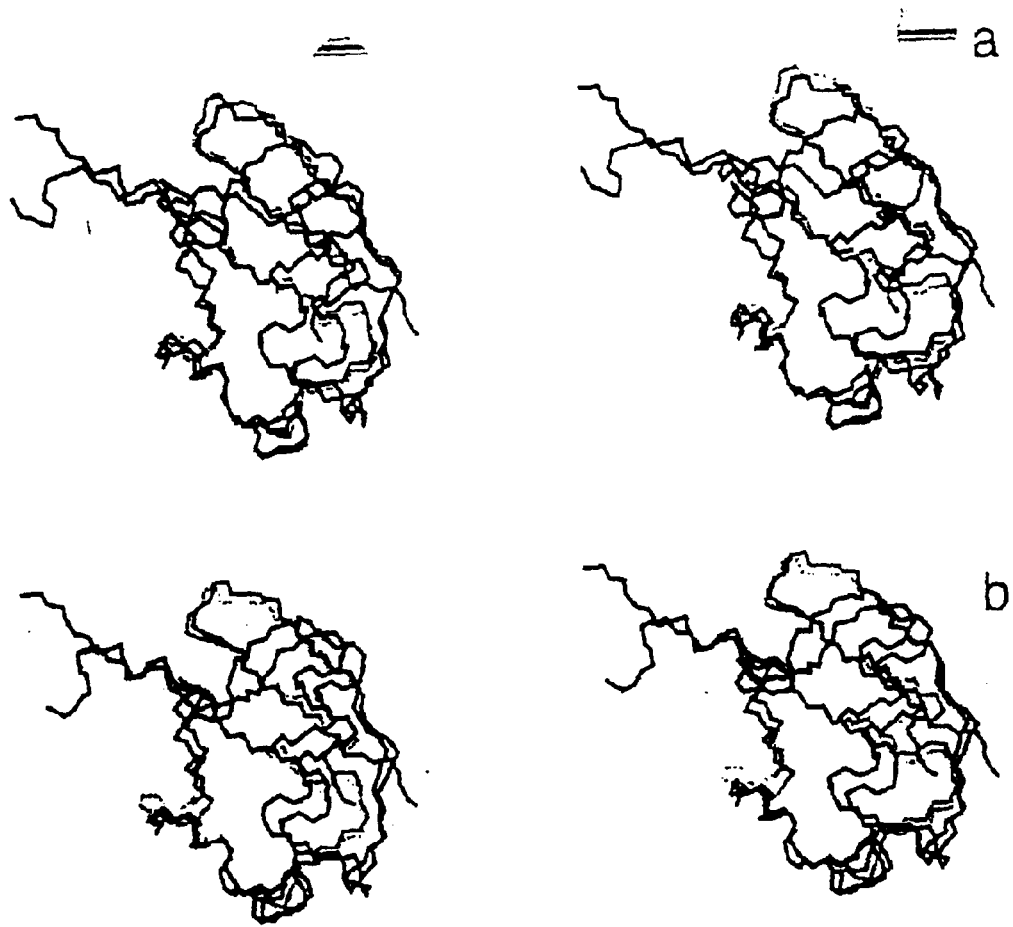
FIG. 6 is a set of stereoscopic images of the global fold of residues 3–73 of ubiquitin.

In most cases, a single pair of $\phi,\psi$ values is compatible with the measured couplings in accord with theoretical predictions is obtained (see FIGS. 5A and 5B). However, in certain instances, two or more minima can be observed on the $\phi,\psi$ surface that have very similar energies (FIG. 5C). Such ambiguities can arise from a number of sources, including absent data for certain residues, coincidences between bond vector and tensor orientations or limitations in the accuracy of experimental residual dipolar couplings. These ambiguities usually can be resolved by consideration of the known sensitivity of the C$\alpha$ chemical shift of a given residue to the conformation about $\phi$ and $\psi$. See Beger and Bolton, *J. Biol. NMR* 10:129–142, 1997, the disclosures of which are hereby incorporated by reference. In the case of ubiquitin, using the residual dipolar couplings described by Ottiger and Bax (*J. Am. Chem. Soc.* 120:12334–12341, 1998), 40 $\phi,\psi$ pairs could be determined unambiguously, and a further 23 pairs could be determined by consideration of C$\alpha$ chemical shifts. A number of $\phi,\psi$ pairs could not be determined unambiguously due to insufficient data (residues M1, Q2, T9, I36, P37, P38, D52, R74) or lack of chirality (glycine residues). In general, the residues having insufficient data were located in loop regions of the protein. The relevant data are summarized in Table I, below.

In circumstances where two or more minima are observed on the $\phi, \psi$ surface, as happens when there is a lack of chirality (glycine residues) or due to enforced or deliberate reduction in the number of available dipolar couplings, the correct minimum and hence the correct $\phi, \psi$ values and dipeptide orientation can be determined as follows. The global fold of a peptidic molecule having a sequence of three or greater amino acids can be determined as described above (with the steps of (a) providing the molecule in a form which is substituted on the backbone with an isotope selected from the group consisting of $^{13}$C, $^{15}$N, and both $^{13}$C and $^{15}$N; (b) subjecting the substituted molecule to NMR analysis in a non-aligned medium; (c) assigning the molecule by computer based on the NMR analysis; (d) placing the molecule in a first state of partial alignment and measuring residual dipolar couplings for the molecule in the first state of partial alignment, wherein the magnitudes and orientations of the principle axes of the alignment tensors for the first state of partial alignment are known or obtained; (e) placing the molecule in a second state of partial alignment and measuring residual dipolar couplings for the molecule in the second state of partial alignment, wherein the magnitudes and orientations of the principle axes of the alignment tensors for the second state of partial alignment are known or obtained; (f) varying computationally by increments the $\phi,\psi$ angles for a first amino acid of the molecule; (g) minimizing the rigid-body orientation of the first amino acid and a second amino acid adjacent in the peptidic sequence to the first amino acid with respect to both tensor frames simultaneously; (h) calculating the minimum difference between measured and calculated dipolar couplings for each of the first and second amino acids; (i) deriving the $\phi,\psi$ angles and orientation of the dipeptide fragment composed of the first and second amino acids; and (j) repeating steps (f)–(i) for each sequential dipeptide fragment of the molecule to obtain a global fold of the peptidic molecule) but with the addition that the atomic coordinates of each dipeptide fragment at the minima are stored in electronic form for not only the lowest energy minimum $\phi,\psi$ configuration, but for a number of other configurations corresponding to additional energy minima on the $\phi,\psi$ surface. Storage of the coordinates of ten total energy minima generally is sufficient and preferred, however the method may be used with storage of any number of the lowest energy $\phi,\psi$ minima, for example about 2 to about 20 of the lowest energy minima, preferably about 5 to about 12 minima and most preferably about 8–10 minima.

Figure 8:
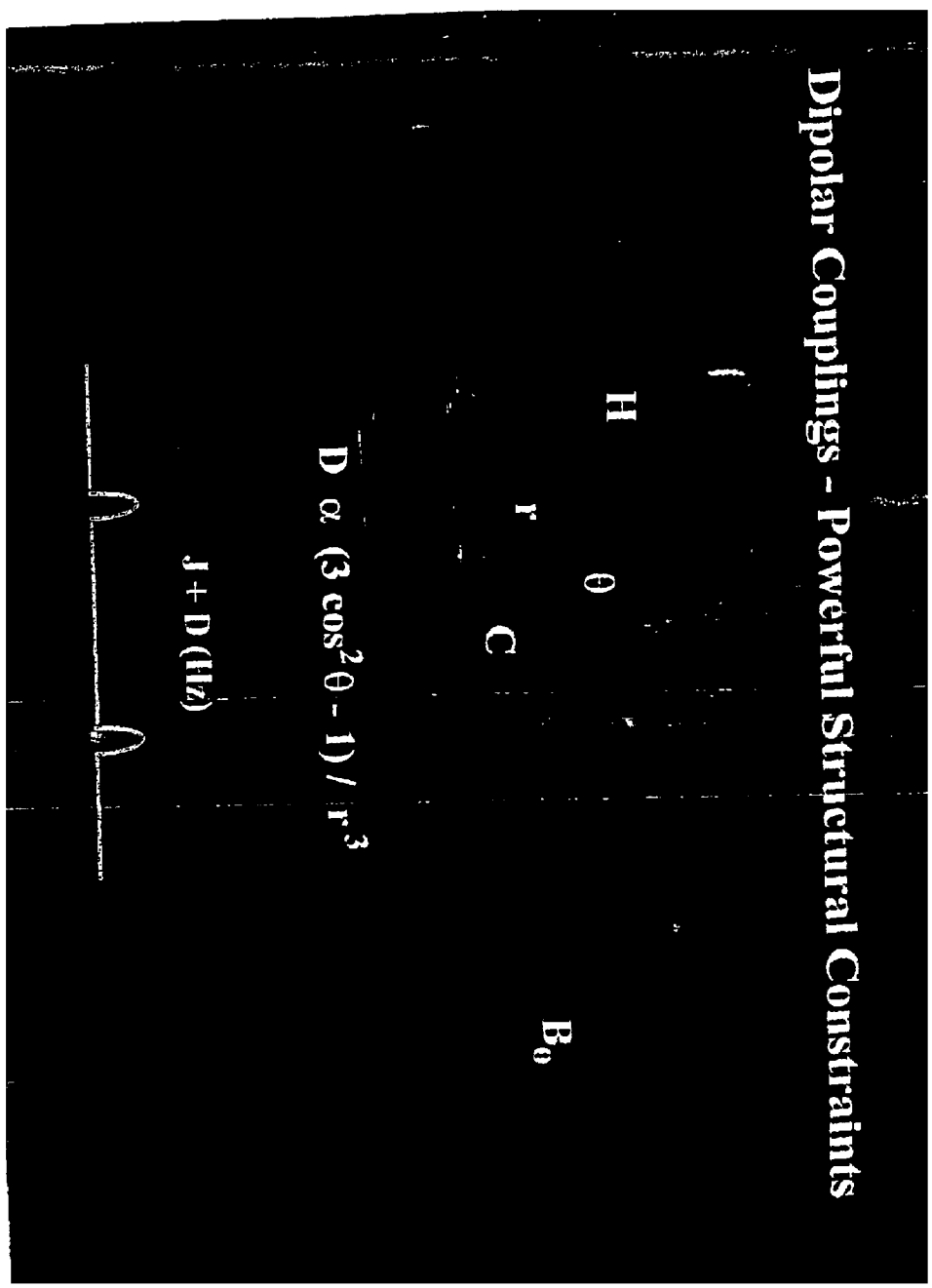
FIG. 8 is a schematic diagram demonstrating calculation of a bond angle.

Each coordinate set is given a unique identification number, which orders the stored coordinate sets according to the minimum energy value at that point on the $\phi,\psi$ surface. The coordinates for a given dipeptide fragment then are compared by translational (but not rotational) root mean square fitting of the coordinates of overlapping atoms from each stored coordinate set for the next dipeptide fragment of the protein sequence. To improve the efficiency of the algorithmic method, it is preferred to assume that the lowest energy coordinate set of the stored coordinate sets has the highest probability of being the correct coordinate set, and thus compare these first. The process is continued with the next lowest energy coordinate set until a good match is obtained as determined by a root-mean-square difference that typically is better than 0.1. See FIG. 8. The resulting composite coordinate set (coordinate set that matches between two adjacent dipeptide fragments) then is used as input to dynamic simulated annealing calculations in the manner described below with regard to FIGS. 5E–5G and 6, together with a limited number of NOE distance restraints as described below and in Example 1.

Thus, the protocols for simulated annealing calculations and for NOE distance restraint calculations can be performed separately, or preferably can be performed in combination. The latter preferred method is readily applicable in circumstances where no chirality information is available. Such information can be difficult to obtain in larger proteins, whereas when the coordinate sets of adjacent dipeptide fragments of the protein are stored for comparison, no additional dipolar coupling information is required to resolve chirality, and the global fold of a protein of any size can be determined to the same effective accuracy using a smaller number of experimental dipolar coupling restraints.

In principle, knowledge of all $\Phi,\psi$ pairs is sufficient to determine the global fold of the protein. However, in structure calculations using the subset of $\phi,\psi$ pairs given in Table I, global fold could not be obtained with prior art methods without distance information due to lack of dihedral angle data for loop regions in the protein.

Since residual dipolar coupling data contain no translational information, there are insufficient structural restraints from these dipolar coupling data alone to generate a unique fold. Therefore, a limited number of NOE distance restraints, namely $H^N$—$H^N$ NOEs, in addition to the dihedral restraints listed in Table I, were incorporated in simulated annealing calculations as described in Example 1. During the course of these calculations, several $H_i^N$—$H_{i+1}^N$ NOEs restraint violations greater than 0.5 Å (S20–D21, D32–G35, E34–D35, D39–Q40) were noted, with corresponding $\phi,\psi$ restraint violations. For each of these violations, comparison of the restrained values of $\phi,\psi$ (Table I) with the corresponding values in the crystal structure, indicated that for certain residues (S20, E34, G35 and D39), incorrect $\phi,\psi$ values were predicted by the residual dipolar couplings.

TABLE I

Values of φ and ψ Derived from Residual Dipolar Couplings in Ubiquitin.

| Residue | Dihedral angles | | Residue | Dihedral angles | | Residue | Dihedral angles | | Residue | Dihedral angles | |
|---|---|---|---|---|---|---|---|---|---|---|---|
| | φ | ψ | | φ | ψ | | φ | ψ | | φ | ψ |
| M1 | n/a | n/a | S20*§ | −80 | 180 | D39§ | −60 | 120 | D58* | −50 | −30 |
| Q2 | n/a | n/a | D21 | −80 | 150 | Q40 | −100 | −20 | Y59 | −100 | 0 |
| I3 | n/a | n/a | T22* | −80 | 170 | Q41 | −90 | 130 | N60 | 60 | 45 |
| F4* | −120 | 140 | I23* | −70 | −60 | R42 | −120 | 120 | I61 | −80 | 110 |
| V5 | −130 | 110 | E24* | −80 | −60 | L43 | −100 | 130 | Q62 | −100 | 160 |
| K6* | −100 | 130 | N25 | −70 | −40 | I44* | −120 | 150 | K63 | −50 | 140 |
| T7 | −100 | 160 | V26 | −60 | −60 | F45 | −150 | 120 | E64 | 70 | 30 |
| L8* | −100 | −30 | K27 | −50 | −40 | A46 | 70 | 60 | S65 | −90 | 150 |
| T9 | m | m | A28 | −60 | −30 | G47 | m | m | T66 | −110 | 130 |
| G10 | m | m | K29 | −70 | −40 | K48* | −120 | 150 | L67 | −120 | 160 |
| K11 | −90 | 140 | I30* | −80 | −40 | Q49* | −85 | 140 | H68 | −120 | 150 |
| T12* | −120 | 130 | Q31 | −60 | −40 | L50* | −80 | 140 | L69* | −100 | 120 |
| I13* | −110 | 120 | D32* | −70 | −40 | E51 | −90 | 140 | V70 | −120 | 150 |
| T14 | −105 | 130 | K33* | −80 | −60 | D52 | m | m | L71 | −90 | 140 |
| L15* | −120 | 160 | E34*§ | −110 | 180 | G53 | m | m | R72 | −100 | 120 |
| E16 | −100 | 120 | G35*§ | −80 | −30 | R54 | −110 | 160 | L73 | −120 | 110 |
| V17 | −135 | 170 | I36 | m | m | T55* | −100 | 160 | R74 | n/a | n/a |
| E18 | −110 | 130 | P37 | — | m | L56 | −60 | −40 | G75 | n/a | n/a |
| P19 | — | −50 | P38 | — | m | S57* | −60 | −30 | G76 | n/a | n/a |

*Value determined from two or more minima on the potential surface, resolved by consideration of Cα chemical shift.
m Multiple minima on φ, ψ surface, not resolvable by consideration of Cα chemical shift.
§Value inconsistent with crystal structure.

In the case of S20 (FIG. 5D), a broad minimum was observed at φ,ψ=−80°, 180°, consistent with the Cα chemical shift. However, the "correct" minimum is located at φ,ψ~−80°, 0°. This can be observed in FIG. 5D, but is 0.7 kcal/mol above the global minimum. The situation is similar for E34 (FIG. 5E), although in this case the "correct" minimum at about φ,ψ −120°, 0° is only 0.16 kcal/mol above the global minimum. For G35, the Cα chemical shift is consistent with an α-helical configuration, but the potential surface is symmetric about φ and ψ due to the lack of chirality information about Cα (FIG. 5F). Finally, for D39, the Cα chemical shift predicts correctly an α-helical configuration, yet two very closely spaced minima are observed near φ,ψ=−40°, 120° (FIG. 5G).

While these discrepancies were clearly detectable from dihedral and NOE restraint violations, the goal of this invention is to generate accurate global folds for proteins without any reference to crystal structure data. The structure calculation protocol therefore was repeated according to the invention, with deletion of the φ,ψ restraints corresponding to these violations. This structure calculation (determined from $N_i$—$H_i^N$, $C_i^\alpha$—$H_i^\alpha$ and $H_i^N$—$C'_{i-1}$, residual dipolar coupling and $H^N$—$H^N$ NOE restraints) gave rise to a global fold whose backbone RMSD for the lowest energy structure of 20 structures was 2.28 Å with respect to the crystal structure (residues 3–73, FIG. 6 and Table II).

TABLE II

Structure Quality for the Global Fold of Ubiquitin.

| | initial | refined |
|---|---|---|
| Measures of Structure Quality | | |
| $E_{L-J}$ (kCal mol$^{-1}$)[1] | 97 (+81 − 36) | 58 ± 9 |
| Coordinate Precisions[2] (Å) | 1.6 | 0.8 |
| Backbone rmsd of Lowest Energy Structure[3] (Å) | 2.28 | 1.8 |

TABLE II-continued

Structure Quality for the Global Fold of Ubiquitin.

| | initial | refined |
|---|---|---|

[1]$E_{L-J}$ = average Lennard – Jones energy calculated using XPLOR **** protein parameters.
[2]Average rms difference between the 20 final simulated annealing structures and the mean coordinates. The values given relate to residues 3–73.
[3]The values given relate to residues 3–73.

Inclusion of residual dipolar coupling data in the form of biharmonic φ,ψ restraints in the manner described above does not directly include information on the orientation of each dipeptide fragment with respect to the tensor frames. This information is of course available from residual dipolar coupling measurements, and can be re-introduced by direct refinement of the global fold obtained above against residual dipolar couplings, in a manner analogous to that described by Tjandra et al. (*Nature Str. Biol.* 4:732–738, 1997), but with fixed, rather than floating tensor-frame orientations.

In the initial stages of the simulated annealing protocol, strong biharmonic restraints were applied corresponding to known values of φ,ψ, which were slowly reduced to zero during the cooling stage with concomitant increase in direct residual dipolar coupling restraints (see Example 1). This refinement protocol gave rise to a global fold whose backbone RMS for the lowest energy structure of 20 structures was 1.8 Å with respect to the crystal structure (residues 3–73, FIG. 7 and Table II).

One unexpected observation was that the five residual dipolar couplings $N_i$—$H_i^N$, $N_{i+1}$—$H_{i+1}^N$, $C_i^\alpha$—$H_i^\alpha$, $H_i^N$—$C'_{i-1}$, $H_{i+1}^N$—$C'_i$ observed in a dipeptide fragment can, for certain residues, be consistent with values of φ and ψ that are clearly incorrect, based on the crystal structure of ubiquitin. In this example, such inconsistencies were obvious from NOE and dihedral restraint violations and thus would be detected even in cases where a crystal structure was not available.

In the case of S20 and E34, the correct φ,ψ values correspond to a minimum on the potential surface, but not the global minimum. In both of these cases, the Cα chemical shift predicts incorrectly that the global minimum φ,ψ values are the correct ones. Notably, the correct φ,ψ values for S20 and E34 are predicted correctly if additional dipolar restraints between $C\alpha_i$—$C'_i$ and $N_{i+1}$—$C'_i$ are included in the gridsearch procedure, suggesting that the discrepancies are due to limited data. In contrast, φ,ψ values for D39 are not correctly predicted even with these additional residual dipolar. restraints. In the study of Wand et al. (*Biochemistry* 35:6116–6125, 1996) the $S^2$ value for D39 is reported to be very low (0.56), on the basis of $^{13}C\alpha$ relaxation data. An implicit assumption in the present work is that all residues possess a uniform $S^2$ value.

Despite the lack of φ,ψ restraints for certain residues due to the factors discussed above, it is clear from the results in Table II that it is possible to determine the global fold of ubiquitin to an accuracy of approximately 1.8 Å backbone RMSD using an average of six dipolar coupling restraints (three in each of two tensor frames) and approximately 2 NOE restraints per residue. This degree of accuracy is more than adequate for use in databases of structural motifs, and provides a method for the determination of protein global folds using conformational restraints derived from backbone atoms only. This method therefore obviates the need to undertake the time-consuming task of sidechain assignment, resulting in an enormous time and labor savings. In contrast to previously available methods, highly accurate protein structural information can be obtained rapidly using a far smaller data set. The small size of the data set used with the inventive methods is an important factor, but in addition, the precise nature of the data obtainable with appropriately isotopically substituted (backbone labeled) proteins allows automation of the process, which was not feasible before. Thus, the methods described here represent an advance in the art which allows both rapid and accurate determination of protein global fold.

Whether a particular level of accuracy can be achieved in a particular case depends on a number of factors. First, the $C_1^\alpha$—$H_i^\alpha$ residual dipolar coupling is very important since it provides information on chirality, and the φ,ψ potential surface displays C2 symmetry in its absence. Wang et al. *J. Am. Chem. Soc.* 120:7385–7386, 1998. This coupling is difficult to measure in larger proteins due to the efficient dipolar relaxation between directly bonded $C^\alpha$—$H^\alpha$ pairs. When these coupling data are not available, however, the $C^\alpha_i$—$C^\beta$ residual dipolar coupling can be used as an alternative source of chirality information. Advantageously, the $C^\alpha_i$—$C^\beta$ residual dipolar coupling can be measured without the need to assign the $C^\beta$ atoms.

Second, in proteins containing a high α-helical content, the long-range $H^N$—$H^N$ NOE restraints required for packing of secondary structural elements may not be available in all cases, and backbone-sidechain or sidechain-sidechain NOEs may be important for determination of global folds. A small number of such NOEs is sufficient for the success of the inventive methods, however. For example, parts of the global fold of *E. coli* acyl carrier protein were derived using residual dipolar coupling measurements together with one backbone-backbone, but the technique also required four backbone-sidechain NOES.

The global fold of *Rhizobium leguminosarum* NodF protein was determined with low resolution using five backbone-backbone NOES and additional data. Fowler et al., *J. Mol. Biol.* 304:447–460, 2000. Clearly, the use of NOEs involving sidechain atoms requires the assignment of the sidechain atoms, which significantly increases the time required to derive the global fold. However, since the number of NOEs required is small in the inventive methods, the effort required for assignment can be reduced by careful choice of isotopic substitution strategies based upon residue type. Therefore, the methods include use of proteins which may be universally isotopically labeled with $^{13}C$, $^{15}N$ or both $^{13}C$ and $^{15}N$ in one or more species of amino acid (one residue type, for example, leucine, valine or isoleucine). Proteins which are universally isotopically labeled with $^{13}C$, $^{15}N$ or both $^{13}C$ and $^{15}N$ on only a single amino acid in the sequence, or two or more amino acids, also are contemplated for use with the invention. Any convenient method may be used for isotopic substitution of proteins and peptides, and such methods are known to those of skill in the art.

To summarize, the general protocol (see flowchart in FIG. 7) for obtaining a global fold (defined as the complete three dimensional structure of the protein backbone) according to the invention is as follows:

1. A protein is selected for study and synthesized with backbone only isotopic substitution with $^{13}C$, $^{15}N$, or both $^{13}C$ and $^{15}N$ and optional isotopic substitution with $^2H$ at the Cα position protons. This isotopic substitution allows the determination of global folds of the largest possible proteins due to improvement in the NMR data that are thereby obtained.

Figure 9:
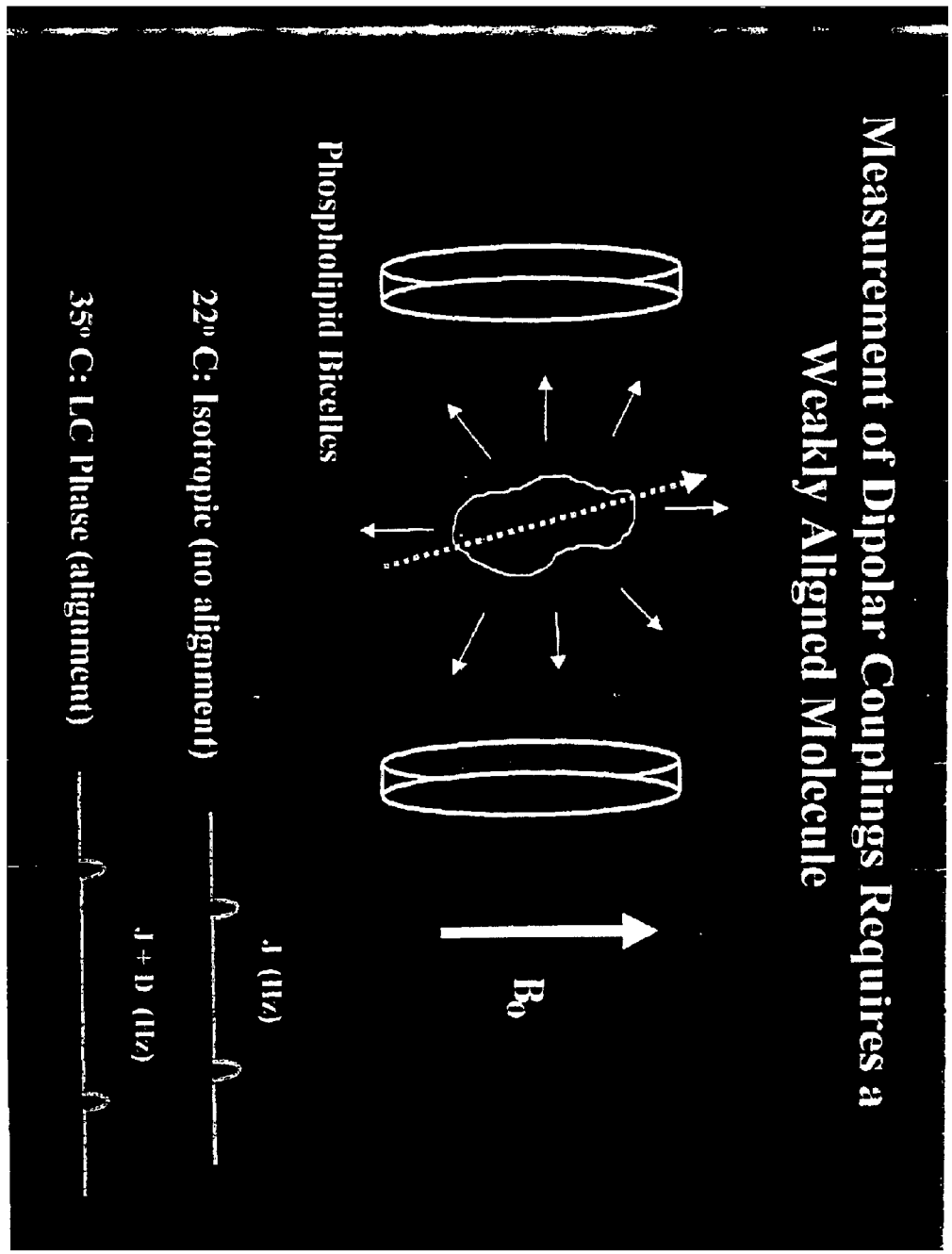
FIG. 9 is a schematic diagram showing measurement of dipolar couplings assisted by weakly aligning the molecule under study.

2. The protein is subjected to NMR spectroscopic analysis in an aqueous (non-aligned) solution. See FIGS. 8 and 9. The term J is measured as the distance between split peaks in non-aligned medium. This distance represents both D and J when measured in aligned media. D can be calculated from measurement in aligned and non-aligned media (see FIG. 9). The equation then can be solved for θ, however there is more than one solution to the equation.

3. The protein is assigned by computer, taking advantage of the substantial sensitivity and resolution gain available from the backbone labeling protocol. Assignment is the identification of which signal in the NMR data comes from which atom in the molecule being assayed. Because the NMR data used is very clean and precise, with sharp peaks and little splitting, this process is much simpler and can be performed by computer, unlike previous methods. The method may involve identification of the N-terminal nitrogen (—$NH_2$), then the adjacent Cα, then the next atom (the carbonyl carbon) and so on, walking along the backbone of the peptide sequence. Ikura et al., Biochemistry 29:4659–4667, 1990.

4. Residual dipolar couplings are measured for the protein in two different partially aligned states, for example in two different liquid crystalline solutions. This allows unambiguous solution of Equation I to obtain a calculated θ angle for each bond. Three, four, five or more residual dipolar couplings may be measured in each partially aligned state (tensor frame). Preferably, three residual dipolar couplings are sufficient.

5. The magnitudes and orientations of the principal axes of the alignment tensors are obtained for each partial alignment (e.g. each liquid crystalline solvent) by using any suitable conventional method, such as, for example, matrix diagonalization or grid-search or from published data.

6. Using computational algorithms known in the art, the φ,ψ angles for a given amino acid are independently varied, in 15–5 degree steps. The rigid-body orientation of this amino-acid and the next amino acid in the polypeptide chain is minimized with respect to both tensor frames simultaneously.

7. Using the φ,ψ angles obtained for the secondary structural elements, a three dimensional structure (global fold) is built for the protein, defining these secondary structural elements.

8. The global fold of the protein is refined from the initial structure obtained in step 7 by further use of residual dipolar couplings to align secondary structural elements. Distance restraints derived from NH—NH NOEs also may be employed for this purpose.

Figure 10:
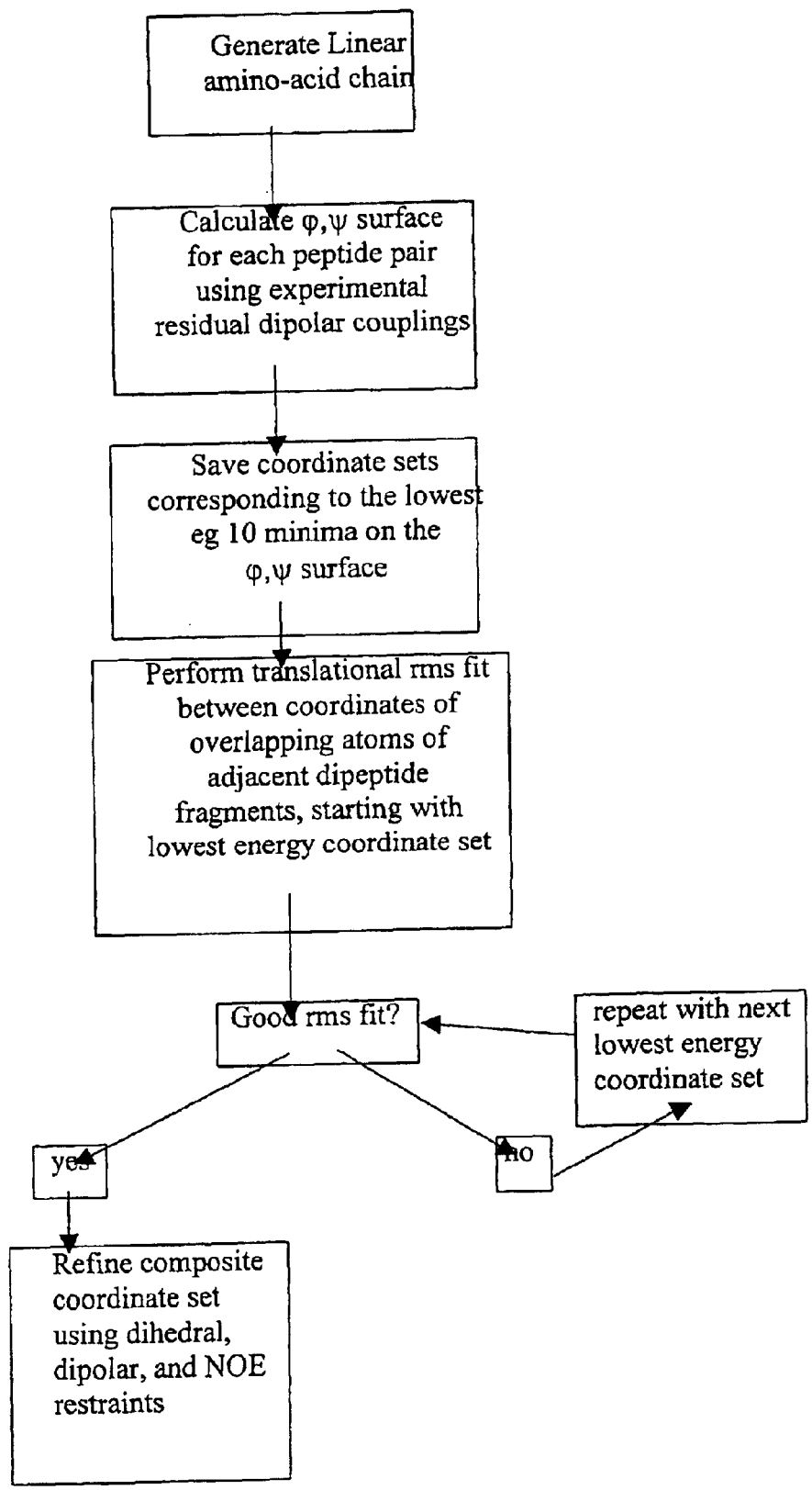
FIG. 10 is a flow chart showing some of the steps of a preferred embodiment of the method of obtaining global fold data.
Figure 11:
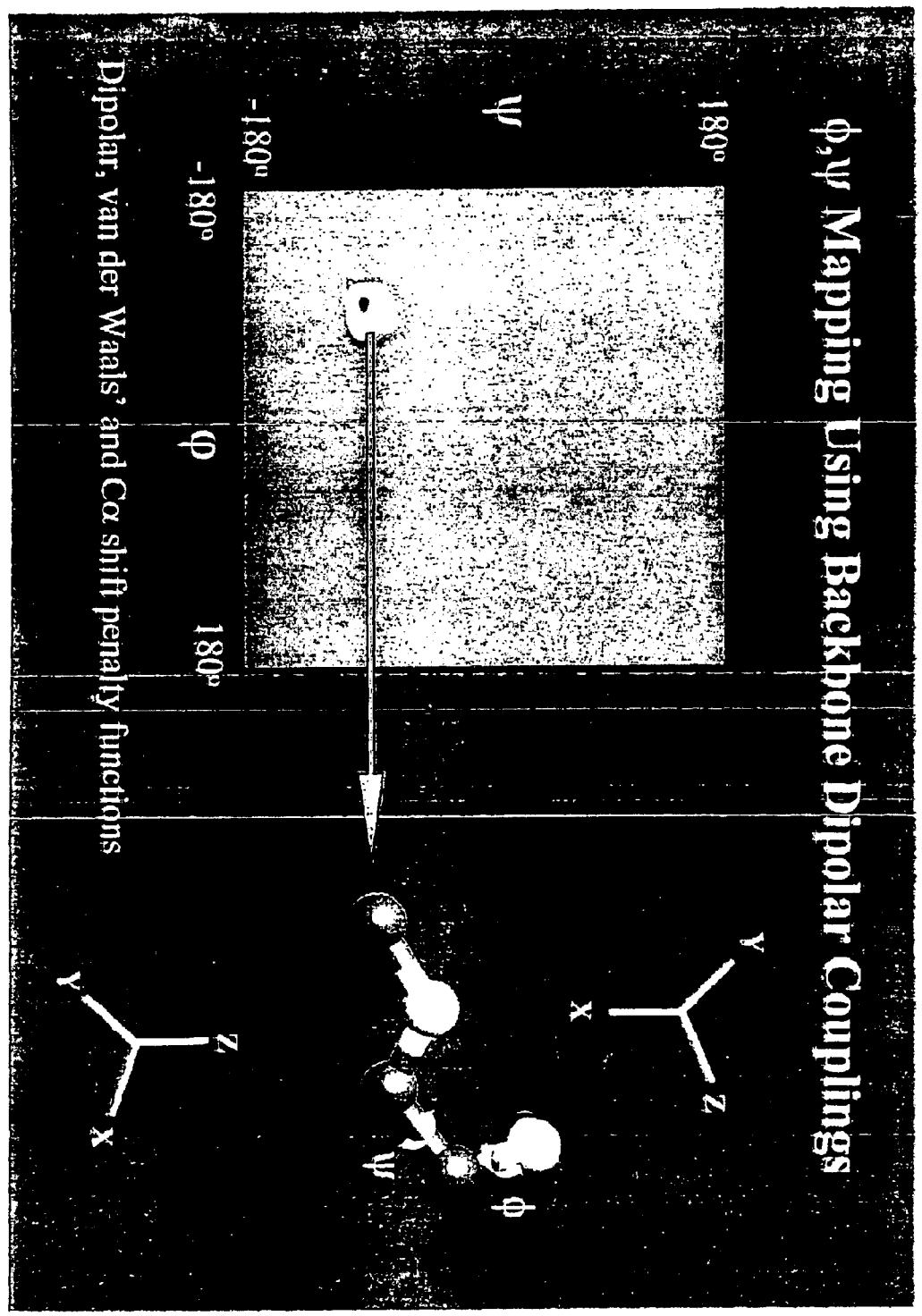
FIG. 11 provides an example of $\phi,\psi$ mapping using backbone dipolar couplings.

Alternatively, instead of using the above method alone to fold the protein according to the determined $\phi$ and $\psi$ angles one amino acid residue at a time using the lowest energy solution of the angles using additional distance information where needed to assist in resolving ambiguities, the coordinates (i.e. the atomic positions) of the atoms in the backbone of the amino acid in the protein for each minimum, which also are available from the same data, are stored and used to determine the orientation of the amino acid fragment in space with respect to the tensor frames. See FIG. 10. In FIG. 11, the orientation of the two tensor frames are represented by the two Cartesian coordinate sets above and below the molecular model showing the peptide fragment. By measuring in two different tensor frames, the orientation of the molecule fragment can be uniquely determined using the inherent properties of the mathematics.

In this way, the values of $\phi$ and $\psi$ are determined as before, and the unique orientation of the fragment is considered as well. Therefore, when ambiguities are present due to multiple solutions to the equation to determine $\phi$ and $\psi$ (multiple minima), the orientation of the fragment can be used to resolve the ambiguity in the structure and determine the correct $\phi$ and $\psi$ angles without having to resort to obtaining distance information. This avoids having to perform an additional step and allows unambiguous determination of the global fold more quickly and easily. Because information is much more likely to be missing in larger proteins, this method makes it possible to determine the structure more accurately even with the inevitable missing information when studying proteins greater than 20 kD or 50–60 kd or larger. The method therefore allows one to obtain accurate global fold information for large proteins which previously had not been obtainable.

Figure 12:
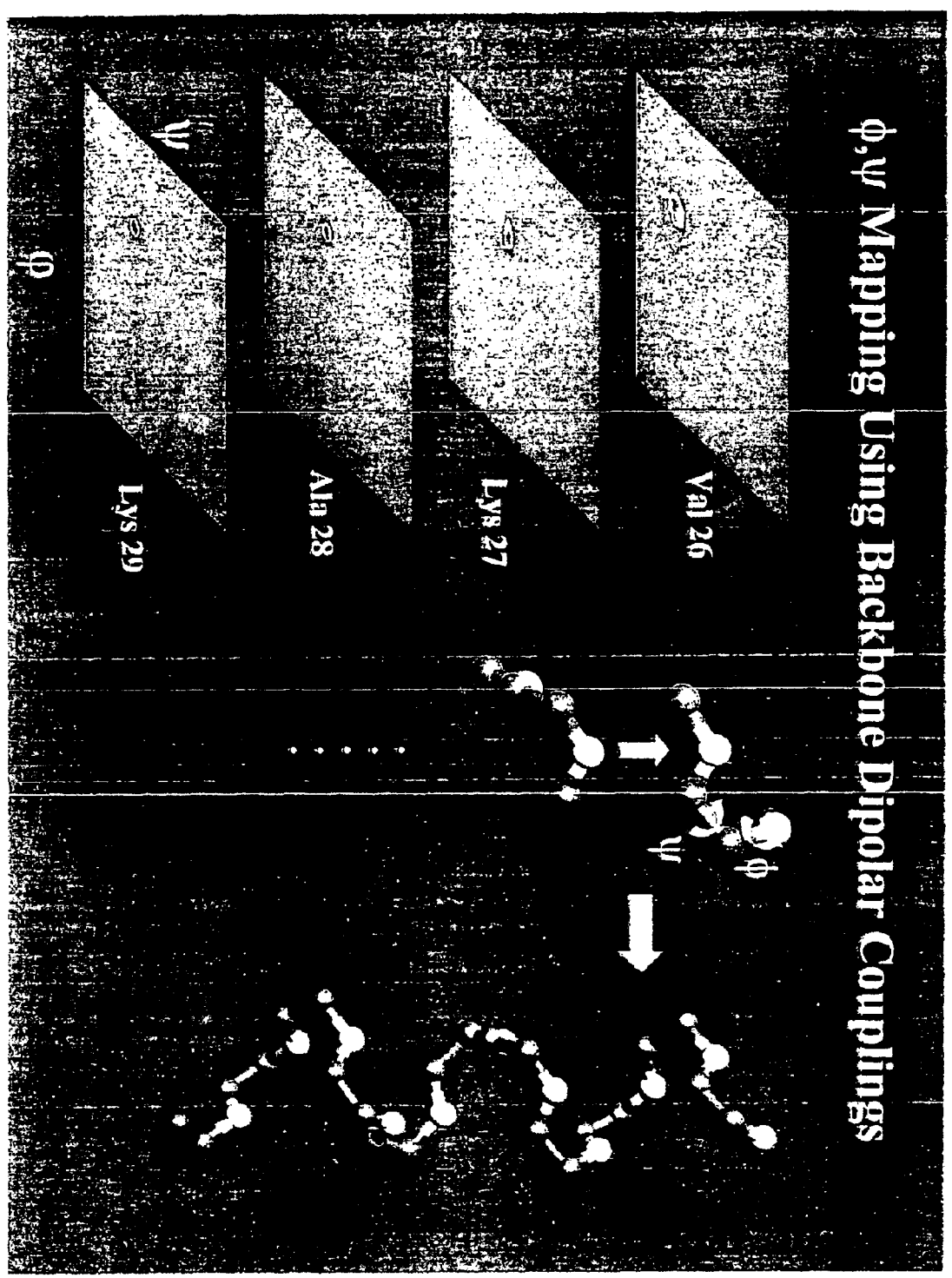
FIG. 12 shows $\phi,\psi$ mapping data using backbone dipolar couplings for a representative dipeptide pair of mouse urinary protein.

When the orientation of each (dipeptide) fragment is determined with respect to the fixed tensor frames, the orientation of each fragment can be compared directly to the orientation of its neighbors since each orientation is determined with respect to the same fixed tensor frame. FIG. 12 shows data for a representative dipeptide pair of mouse urinary protein. The $\phi$ and $\psi$ angles of Val 26 (amino acids 25 and 26) and Lys 27 (amino acids 26 and 27) are represented by the stacked planes, each having a single minimum (dark spot) showing the $\phi$ and $\psi$ angles. To the right, the orientations of the two peptides are represented with molecular models. Because the minimum shown in the plane represents the correct $\phi$ and $\psi$ angles, the orientation of the two adjacent peptides match up. Thus, matching orientations determined for adjacent amino acid pairs can be used to confirm a correct solution for $\phi$ and $\psi$ since the successive pairs along the sequence of the protein overlap. In this case (FIG. 12), the orientation of amino acid 26 is the same when determined for the dipeptide pair of 25/26 and for the dipeptide pair of 26/27, confirming that the solution of $\phi$ and $\psi$ was the correct one.

Figure 13:
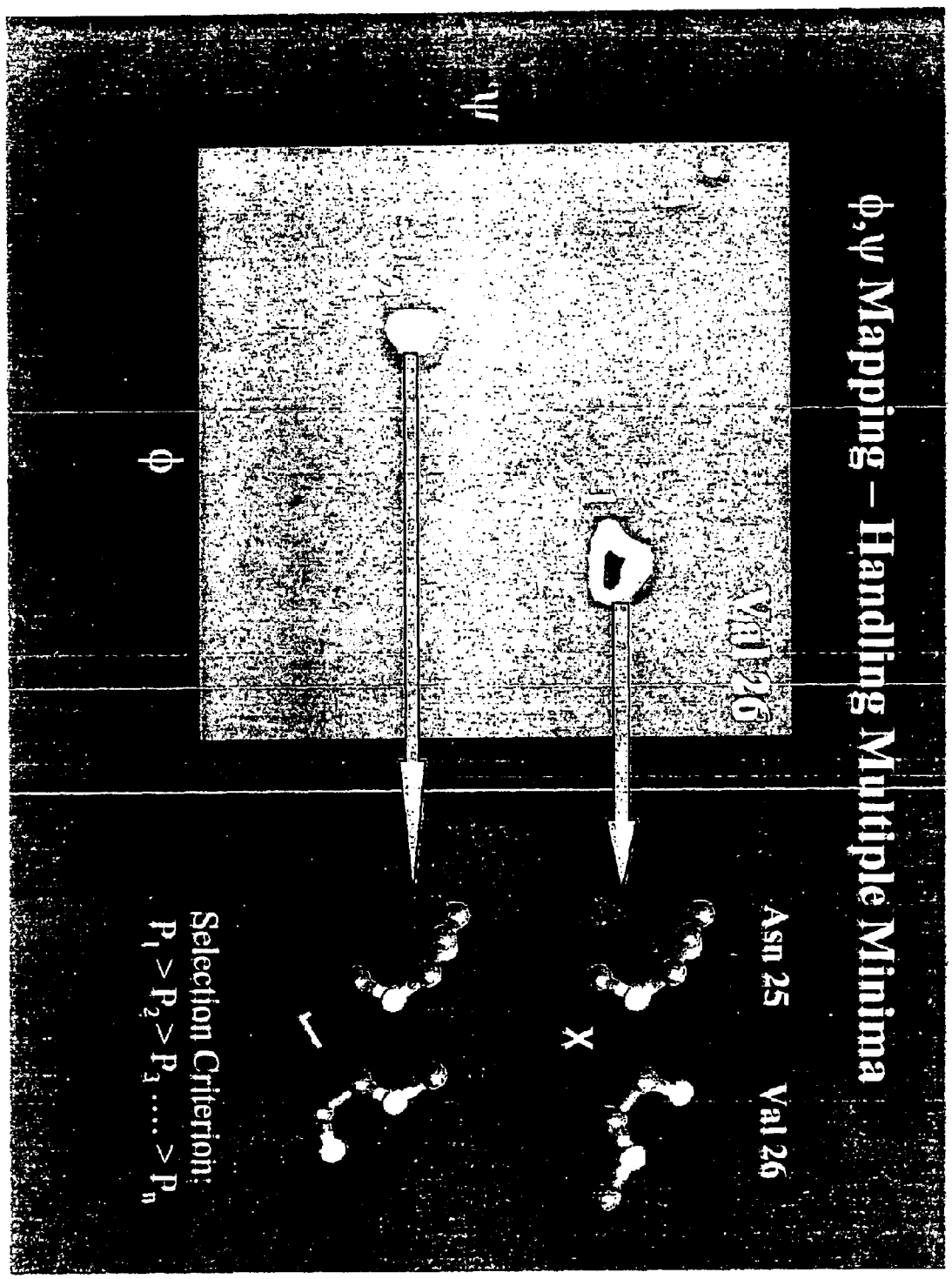
FIG. 13 demonstrates an example of a method to establish whether an energy minimum represents the correct $\phi,\psi$ angles.

Therefore, rather than folding the successive amino acids of a peptide or protein chain using calculated most favorable $\phi$ and $\psi$ angles, successive overlapping pairs of amino acids can be superimposed to form the global fold of the entire chain of amino acids. This method has its greatest advantage when multiple solutions for the $\phi$ and $\psi$ angles are found. For example, FIG. 13 shows that the solution for Val 26 in mouse urinary protein actually has three possible solutions (three minima). The lowest energy solution, labeled "1" in the figure, which one would ordinarily expect to be the correct solution, produces the orientations of residues Asn 25 and Val 26 as shown in the upper pair of molecular models. This solution is not the correct one because the orientations do not match. The second lowest energy solution of $\phi$ and $\psi$, labeled "2" in the figure, is associated with the orientations shown in the lower pair of molecular models. It is apparent that this solution of $\phi$ and $\psi$ is correct because the orientations of the two overlapping peptide pairs match. The global fold therefore may be obtained using $\phi,\psi$ angles which have been confirmed by the orientation information available from the calculations, or may be obtained using $\phi,\psi$ angles and distance information, or may be obtained using overlapping orientations of dipeptide pairs, or may be obtained using a combination of one or more of all these methods.

Figure 14:
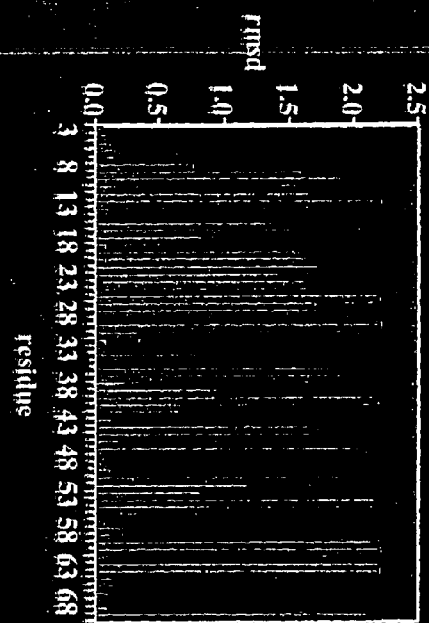
FIG. 14 shows RMSD fitting data for a protein global fold obtained using methods disclosed in the application for fitting of all lowest energy coordinate sets (14A) and fitting of coordinate sets according to $P_1 > P_2 > P_3 \ldots > P_n$.
Figure 14:
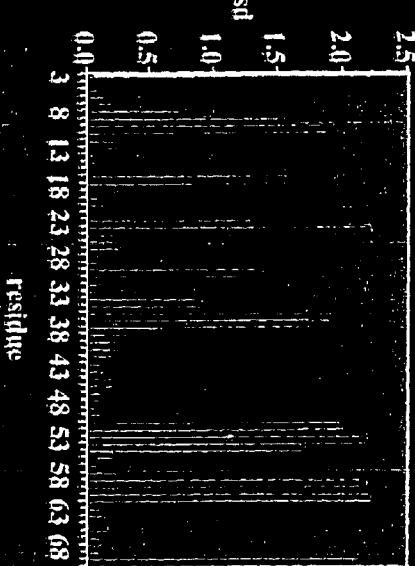

Using prior art methods, generally in this situation either the incorrect $\phi,\psi$ angles would be selected, or the $\phi,\psi$ angles would have to be omitted from the preliminary structure, reducing the accuracy and completeness of the structure. The tremendous advantage of the invention is exemplified in FIG. 14, which shows the root mean square deviation (RMSD) fitting data (the degree to which the two pairs of dipeptides are fitting with respect to each other) for an initial structure of a protein derived from all the lowest energy coordinate sets (14A) and the root mean square deviation fitting data for an initial structure of the same protein obtained by fitting coordinate sets confirmed with orientation data (14B). The higher the RMSD, the worse the fit, therefore it is clear that the initial structure obtained is much superior when orientation data assist in determining the initial global fold.

Figure 20:
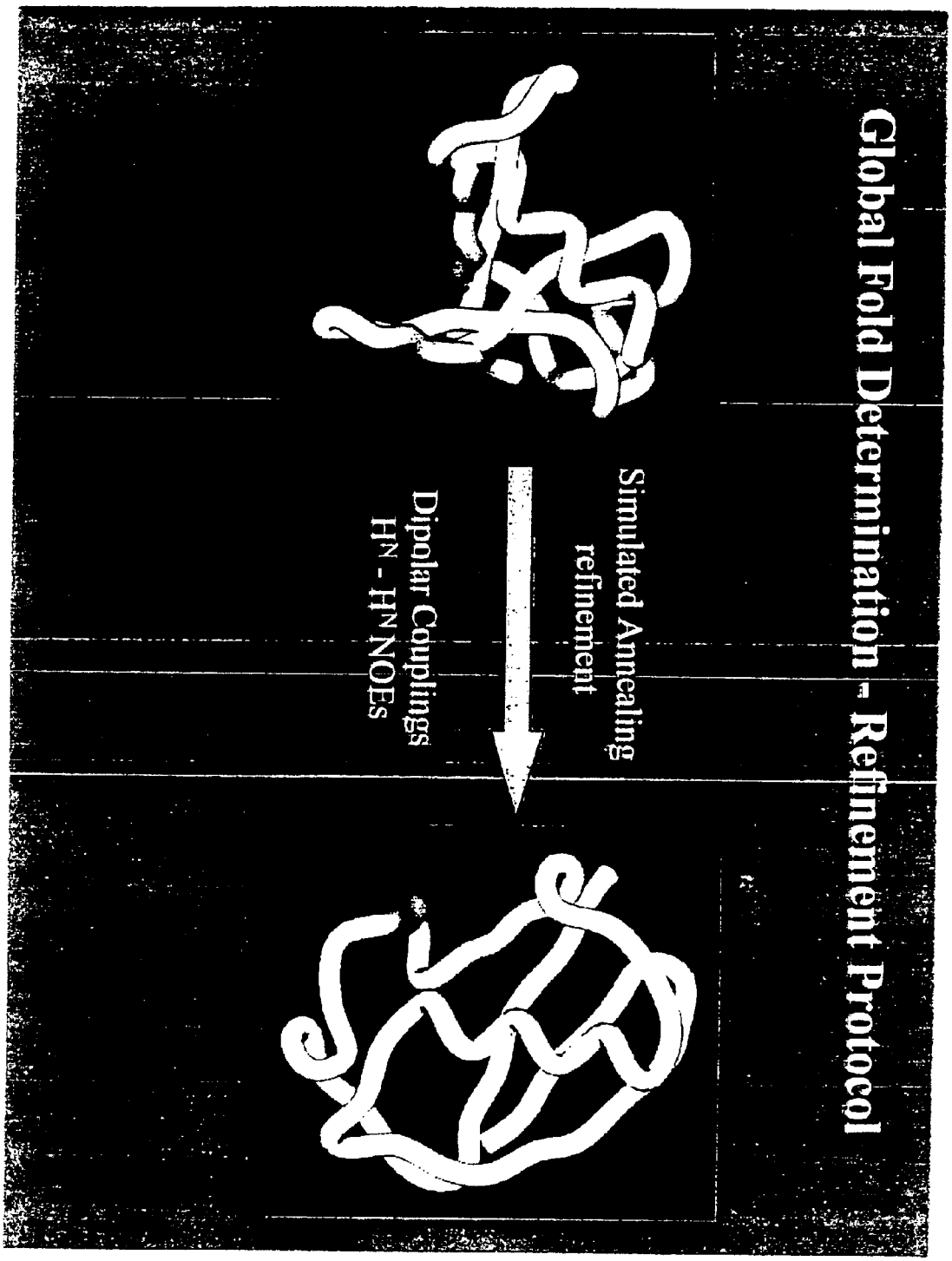
FIG. 20 shows a global fold determination refinement protocol.

Once a preliminary structure is obtained by overlapping orientation of successive peptide pairs along the length of a peptide sequence, the structure is refined, or regularized, by simulated annealing refinement protocol. The preliminary structure is based upon relative orientational information, but does not incorporate translational information. This simulated annealing refinement protocol is a way of building translational information into the structure using the Nuclear Overhauser Effect and dipolar couplings information. See FIG. 20.

The following examples are provided to illustrate rather than to limit the invention claimed herein.

EXAMPLES

Example 1

Derivation of Tensor Frame Orientations

Experimental residual dipolar coupling data in two tensor frames were taken directly from Ottiger and Bax, *J. Am. Chem. Soc.* 120:12334–12341, 1998. $H^N$—$H^N$ NOEs restraints were computed from the crystal structure of ubiquitin using a simple distance matrix approach and including all $H^N$—$H^N$ distances less than 5 Å.

The relative orientations of the tensor frames were calculated using a simulated annealing approach. Each of two idealized α-helices ($\phi$=−57°, $\phi$=−47°) representing fragments K29–E34 (fragment 1) and N25–I30 (fragment 2) of the long ubiquitin helix were used as starting structures for molecular dynamics simulation. Experimentally obtained one-bond $H^N$—N and CαHα dipolar couplings from two different alignment media and simulated $H^N$—N NOE-data were used as restraints in XPLOR simulated annealing refinement protocols. See Ottinger and Bax, *J. Am. Chem. Soc.* 120:12334–12341, 1998 and Brünger, XPLOR, version 3.1: A System For X-ray Crystallography and NMR, Yale University Press, New Haven, Conn., 1987, the disclosures of which are hereby incorporated. The first alignment tensor was fixed in this protocol, while the second tensor and the helical fragment were allowed to reorient in the course of the calculation. By altering the structure and reorientation of the second tensor the $H^N$—N NOEs and the dipolar coupling restraints were satisfied.

A high degree of convergence of the resulting orientation of the second order tensor principal axis system relative to first system and the helical fragment was observed. In total, 379 and 1568 structures and tensor frame orientations were calculated for the helical fragment 1 and fragment 2, respectively. Using straightforward geometry and linear algebra, rotation matrices describing the relative orientation of the two tensor frames were calculated. Euler angles obtained from these rotation-matrices were grouped according to well-known inversion properties of dipolar reference frames (Fowler et al., *J. Mol. Biol.*, 304:447–460, 2000) and used for the calculation of averaged order tensor orientations. XPLOR rigid body minimization protocols and ORDERTEN_SVD (Losenczi et al., *J. Magn. Reson.*, 138:334–342, 1999, the disclosures of which are hereby incorporated by reference) calculations were employed to check for consistency of the obtained structure ensemble and averaged tensor frames with the two sets of residual dipolar couplings. One of the averaged tensor frames was picked at random and used in subsequent calculations of the ubiquitin structure. The orientation of the second tensor frame relative to the first frame is given by the three Euler angles 165°, 171° and 300°.

Example 2

Determination of $\phi, \psi$ Values for Residue Pairs

Figure 15:
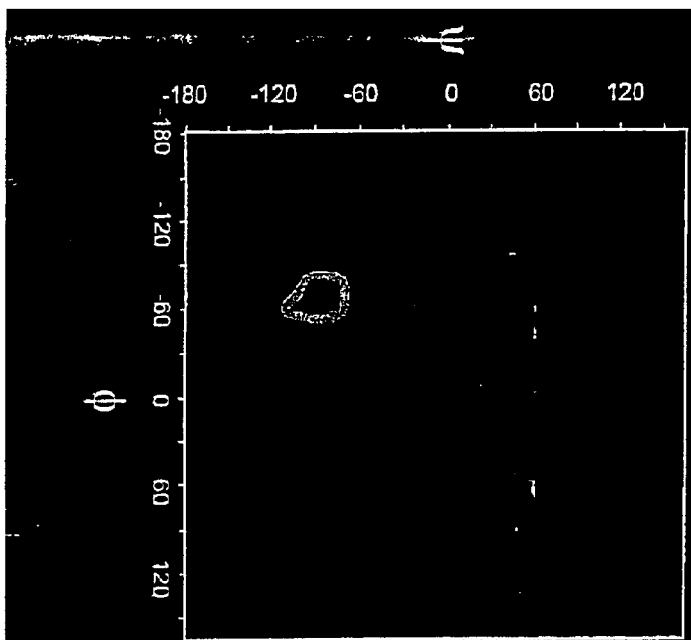
FIG. 15 is a set of contour maps for two residues of ubiquitin as indicated.
Figure 15:
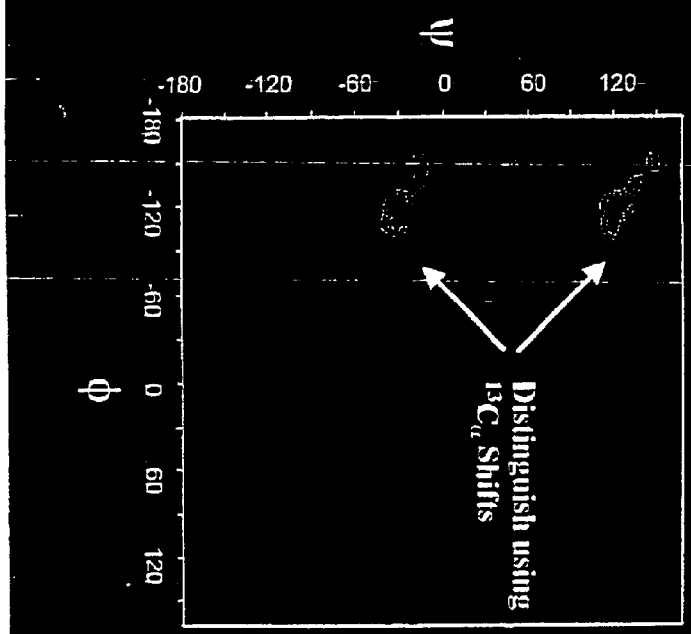
Figure 16:
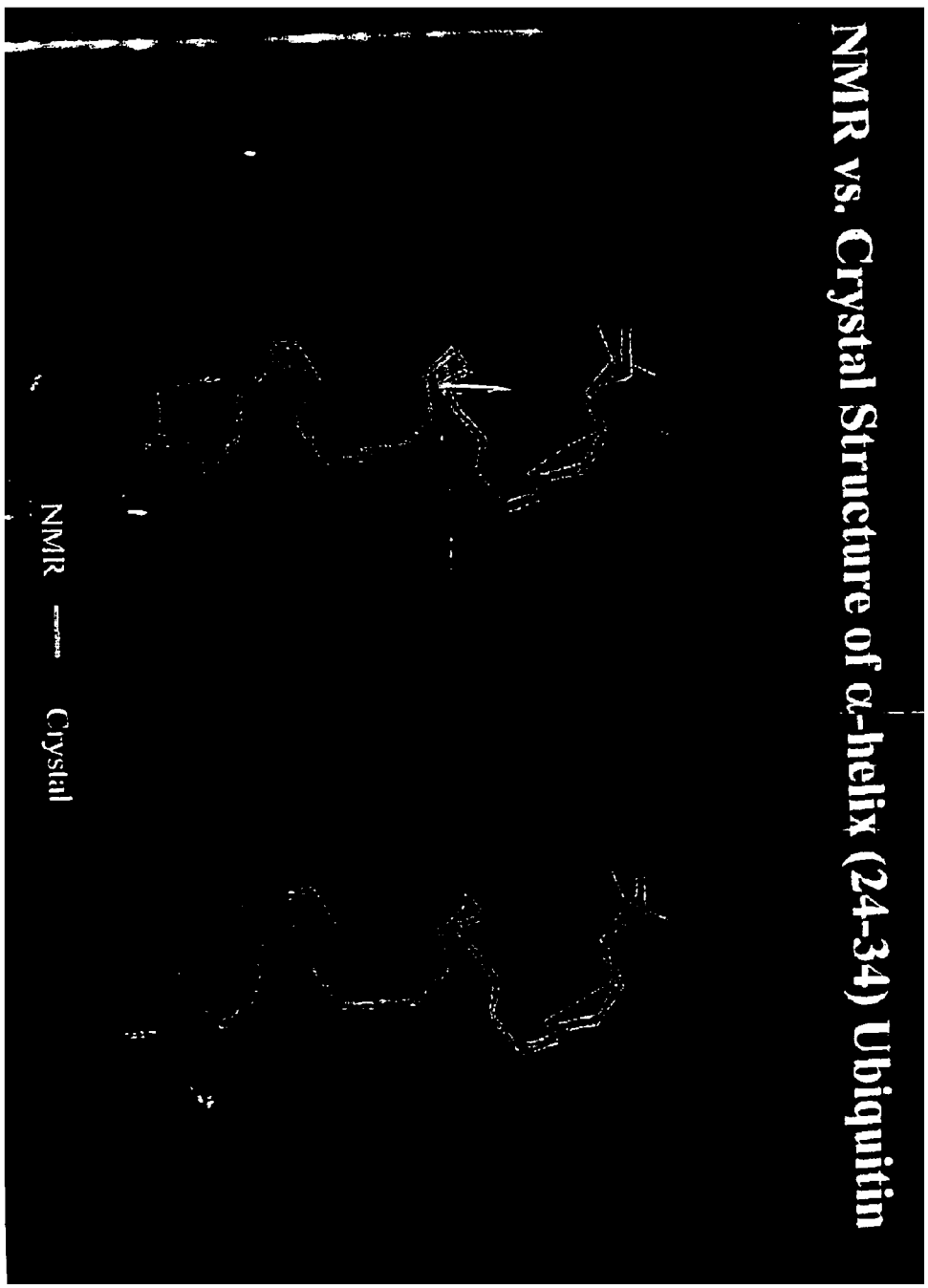
FIG. 16 is a stereoscopic diagram providing the global fold of α-helix (24–34) of ubiquitin, as determined by the inventive methods and by X-ray crystallography.
Figure 17:
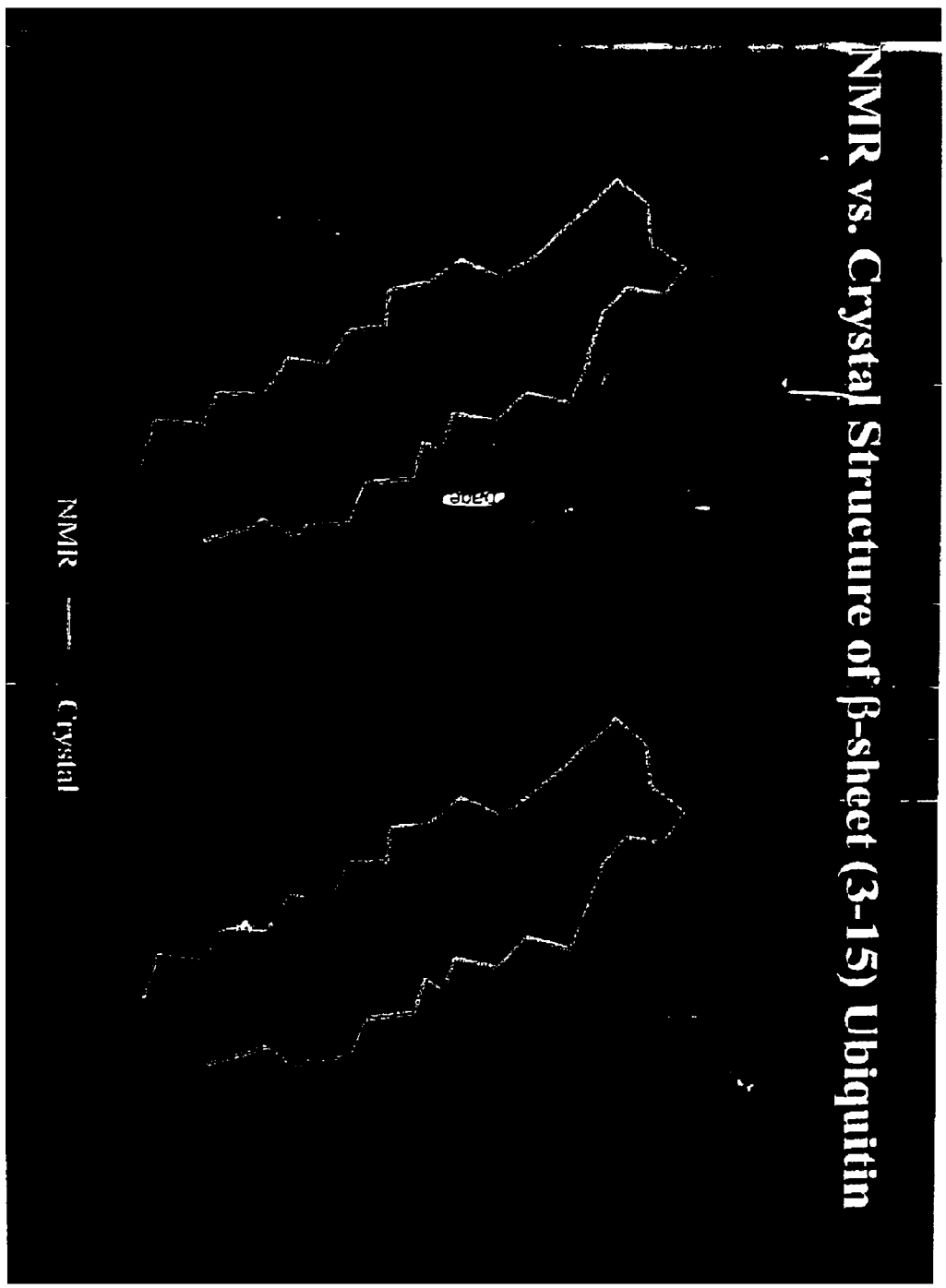
FIG. 17 is a stereoscopic diagram providing the global fold of β-sheet (3–15) of ubiquitin, as determined by the inventive methods and by X-ray crystallography.

Three dimensional $\phi, \psi$ potential surfaces were calculated for ubiquitin using XPLOR version 3.851. First, an extended structure for ubiquitin was generated by setting all $\phi, \psi$ angles to 180° (with the exception of $\phi$ for prolines). Groups of three residues (i−1, i, i+1) were then considered stepwise from the COOH terminus, with the sidechain of residue i truncated at $C^\beta$. The values of $\phi$ and $\psi$ for residue i were each varied independently through 360° in 15° increments, resulting a two dimensional grid of 576 points as in FIG. 4. At each point, a rigid body minimization was performed on the tripeptide fragment to minimize the difference between experimental and theoretical residual dipolar couplings $N_i$—$H_i^N$, $N_{i+1}$—$H_{i+1}$, $C_i^\alpha$—$H_i^\alpha$, $H_i^N$—$C'_{i-1}$, $H_{i+1}^N$—$C'_i$ with respect to two sets of external Cartesian axes whose relative orientation is defined by the two tensor frame orientations determined above. To overcome the effects of local minima during the minimization procedure, the rigid body minimization was performed ten times at each grid point, starting with randomized values of the three Euler angles that describe the orientation of the tripeptide fragment in the tensor frames. See FIG. 15. The axial $A_a$, component and rhombicity R in each tensor frame was taken from Ottiger and Bax, *J. Am. Chem. Soc.* 120:12334–12341, 1998, the disclosures of which are hereby incorporated by reference. Force constants of 0.5, 0.247, and 1.61 kcal mol$^{-1}$ HZ$^{-2}$ were used for N—$H^N$, $C^\alpha$—$H^\alpha$ and $H^N$—C' residual dipolar couplings, respectively. In addition, a weak repulsive van der Waals term was included to account for steric clashes involving the $C^\beta$ atom of residue i. The resulting potential surfaces were contoured automatically using a script written for the program Maple, although any other suitable and convenient program known in the art may be used. See FIGS. 16 and 17.

Example 3

Calculation of Global Fold

The global fold of ubiquitin was determined with $H^N$—$H^N$ NOE restraints and residual dipolar coupling-derived dihedral restraints using the XPLOR simulated annealing script (sa.inp) (Brünger, XPLOR, version 3.1: A System for X-ray Crystallography and NMR; Yale University Press, New Haven, Conn., 1987) with the following differences. Restraints corresponding to values of $\phi$ and $\psi$ for which unique solutions exist could be derived from the plots derived in the gridsearch procedure above. See FIG. 4. Together with consideration of $C\alpha$ chemical shifts as necessary, they were applied as standard biharmonic dihedral restraints. An initial force constant of 200.0 kcal mol$^{-1}$ rad$^{-2}$ was used, rising to 500.0 kcal mol$^{-1}$ rad$^{-2}$ at the end of each simulated annealing run. A total of 6000 molecular dynamics steps of 5.0 fs were computed at a temperature of 1000 K, followed by 3000 cooling steps of 5.0 fs to a final temperature of 100 K. This standard type of method removes a thermal element from the structure in which the intramolecular movements are reduced to near zero. Twenty structures were calculated from an initial starting structure whose $\phi, \psi$ angles were set to those defined by the residual dipolar coupling data where unique values were available. Where the values of $\phi, \psi$ were not available from the residual dipolar coupling data alone, or were ambiguous, these were set to 180° in the starting structure.

Example 4

Refinement of Global Fold

Figure 18:
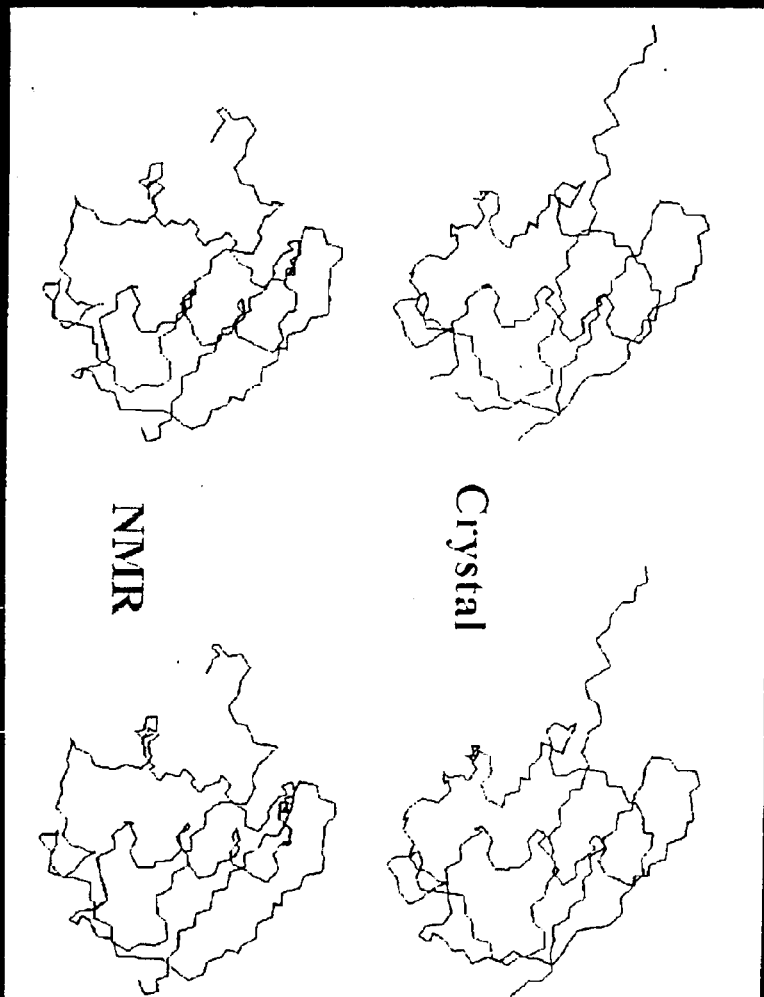
FIG. 18 is a stereoscopic diagram providing the global fold of ubiquitin, as determined by the inventive methods and by X-ray crystallography.

Global fold refinement was performed with the lowest energy structure from the previous set of calculations as input. This initial structure was refined against residual N—$H^N$, $C\alpha$-$H\alpha$ and $H^N$—C' dipolar coupling and $H^N$ NOE data using the XPLOR script sa.inp (Brünger, XPLOR, version 3.1: A System for X-ray Crystallography and NMR; Yale University Press, New Haven, Conn., 1987) with the following differences. In the high temperature phase involving 3000 MD steps of 5 fs at 500 K, dihedral angle restraints were applied as in the previous global fold determination, but with a force constant of 100 kcal mol$^{-1}$rad$^{-2}$. In addition, weak N—$H^N$, $C\alpha$-$H\alpha$ and $H^N$—C' residual dipolar coupling restraints were initially applied with a force constant of 0.02 kcal mol$^{-1}$ Hz$^{-2}$, using two external Cartesian axes whose relative orientation was defined by the two tensor frame orientations determined in Example 1. During the cooling phase of 6000 steps of 1 fs, the dihedral force constant was reduced to zero at the end of the cooling period, with concomitant increase of the residual dipolar coupling force constant to 0.5 kcal mol$^{-1}$ Hz$^{-2}$. Twenty structures were calculated from the initial starting structure. The final structure (structural map) is shown in FIG. 18.

Example 5

Refinement of Global Fold Obtained Using Orientation Data

Figure 19:
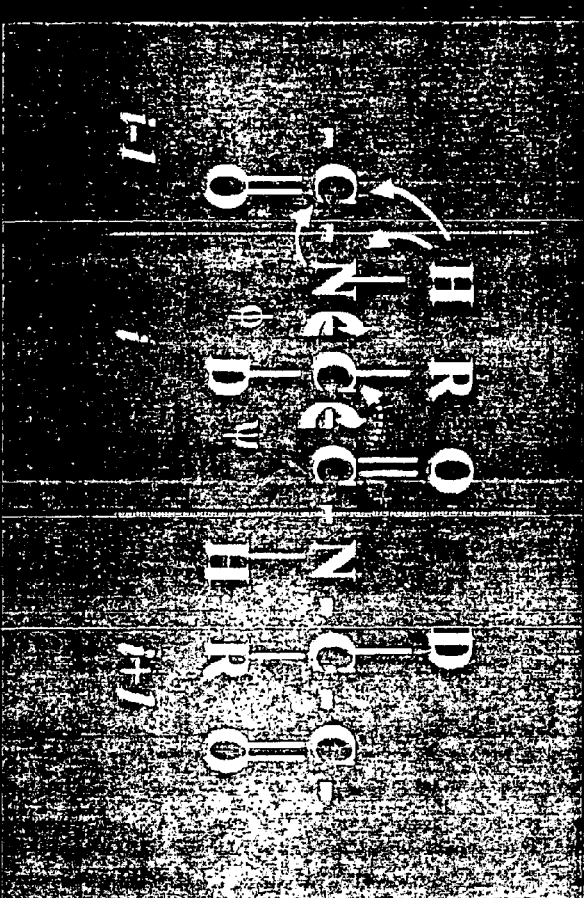
FIG. 19 shows dipolar couplings in an exemplary perdeuterated protein.
Figure 21:
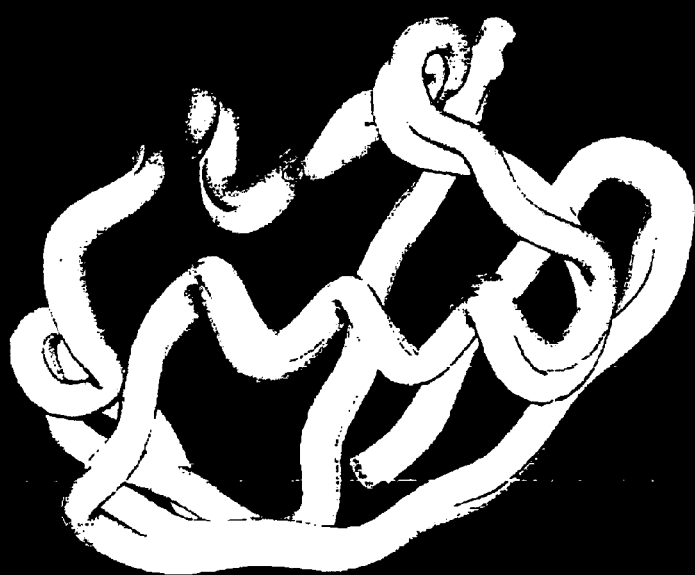
FIG. 21 shows a global fold of ubiquitin obtained by NMR versus crystal structure.

A preliminary structure of ubiquitin was determined by NMR analysis as described in the specification and exemplified in Examples 1 and 2. Orientations of overlapping peptide fragments were superimposed to obtain the structure and to confirm the correct solution of $\phi, \psi$ angles. Three dipolar couplings per residue were measured. See FIG. 19. The three narrow arrows for each amino acid (for a total of six arrows) show the dipolar couplings measured. The dotted arrow shows a dipolar coupling which optionally may be measured as well. The RMSD data for the initial structure obtained in this way is shown in FIG. 14B and the structure itself, having an average backbone RMSD of 1.2 Å is presented in FIG. 21.

What is claimed is:

1. A method for determining the global fold of a peptidic molecule having a sequence of three or greater amino acids which comprises the steps of:

(a) providing said molecule in a form which is substituted on the backbone with an isotope selected from the group consisting of $^{13}$C, $^{15}$N, and both $^{13}$C and $^{15}$N;

(b) subjecting said substituted molecule to NMR analysis in a non-aligned medium;

(c) assigning said molecule by computer based on said NMR analysis;

(d) placing said molecule in a first state of partial alignment and measuring residual dipolar couplings for said molecule in said first state of partial alignment, wherein the magnitudes and orientations of the principle axes of the alignment tensors for said first state of partial alignment are known or obtained;

(e) placing said molecule in a second state of partial alignment and measuring residual dipolar couplings for said molecule in said second state of partial alignment, wherein the magnitudes and orientations of the principle axes of the alignment tensors for said second state of partial alignment are known or obtained;

(f) varying computationally by increments the $\phi, \psi$ angles for a first amino acid of said molecule;

(g) minimizing the rigid-body orientation of said first amino acid and a second amino acid adjacent in the peptidic sequence to said first amino acid with respect to both tensor frames simultaneously;

(h) calculating the minimum difference between measured and calculated dipolar couplings for each of said first and second amino acids;

(i) deriving the $\phi, \psi$ angles and orientation of the dipeptide fragment composed of said first and second amino acids; and (j) repeating steps (f)–(i) for each sequential dipeptide fragment of said molecule to obtain a global fold of said peptidic molecule.

2. The method according to claim 1 which further comprises confirming that the $\phi, \psi$ angles derived in step (i) are correct by matching the orientation of overlapping successive peptide pairs.

3. The method according to claim 1 which further comprises repeating steps (f)–(i) for at least one secondary structural element.

4. The method according to claim 1 which comprises providing said molecule in a form in which the Cα position protons are isotopically substituted with $^2$H.

5. The method according to claim 1, wherein the residual dipolar couplings for said molecule are measured in step (d) in at least two different media which impart a weak alignment to said molecule.

6. The method according to claim 5, wherein said media which impart a weak alignment on said molecule are liquid crystalline solutions.

7. The method according to claim 1 which further comprises additionally performing steps (b) through (j) using said peptidic molecule which has been universally isotopically substituted with $^{13}$C, $^{15}$N, or both $^{13}$C and $^{15}$N in one or more species of amino acid.

8. The method according to claim 7, wherein said peptidic molecule is universally isotopically substituted with $^{13}$C, $^{15}$N, or both $^{13}$C and $^{15}$N in one species of amino acid.

9. The method according to claim 1, which further comprises refining said global fold of said peptidic molecule by including data concerning interatom distances.

10. The method according to claim 9, wherein said data concerning interatom distances is NOE data.

11. A method according to claim 1, wherein at least three residual dipolar couplings are measured for each state of partial alignment.

12. A method according to claim 11, wherein three residual dipolar couplings are measured for each state of partial alignment.

13. A method according to claim 11, wherein four residual dipolar couplings are measured for each state of partial alignment.

14. A method according to claim 11, wherein five residual dipolar couplings are measured for each state of partial alignment.

15. A method according to claim 11, wherein more than five residual dipolar couplings are measured for each state of partial alignment.

* * * * *